US012700488B2

(12) United States Patent

Lettman et al.

(10) Patent No.: US 12,700,488 B2

(45) Date of Patent: Aug. 4, 2026

(54) ARTIFICIAL INTELLIGENCE FOR SOUND DETECTION FROM MEDICAMENT OR TEST DEVICE

(71) Applicant: NOBLE INTERNATIONAL, LLC, Orlando, FL (US)

(72) Inventors: Jeffery A. Lettman, Orlando, FL (US); Joshua Hopkins, Casselberry, FL (US)

(73) Assignee: NOBLE INTERNATIONAL, LLC, Orlando, FL (US)

( * ) Notice: Subject to any disclaimer, the term of this patent is extended or adjusted under 35 U.S.C. 154(b) by 434 days.

(21) Appl. No.: 18/009,078

(22) PCT Filed: Jun. 9, 2021

(86) PCT No.: PCT/US2021/036580

§ 371 (c)(1),
(2) Date: May 30, 2023

(87) PCT Pub. No.: WO2021/252606

PCT Pub. Date: Dec. 16, 2021

(65) Prior Publication Data

US 2023/0215537 A1 Jul. 6, 2023

Related U.S. Application Data

(60) Provisional application No. 63/036,655, filed on Jun. 9, 2020.

(51) Int. Cl.
*G16H 20/17* (2018.01)
*G06N 3/0442* (2023.01)
*G06N 3/08* (2023.01)

(52) U.S. Cl.
CPC ........... *G16H 20/17* (2018.01); *G06N 3/0442* (2023.01); *G06N 3/08* (2013.01)

(58) Field of Classification Search
CPC ........ G16H 20/17; G06N 3/0442; G06N 3/08; G06N 3/09; G06N 3/044; G06N 3/0464;
(Continued)

(56) References Cited

U.S. PATENT DOCUMENTS

| | | | |
|---|---|---|---|
| 9,767,708 B2 | 9/2017 | Baker et al. | |
| 10,599,958 B2 | 3/2020 | He et al. | |
| 2018/0204636 A1* | 7/2018 | Edwards | ................ G16H 40/67 |

FOREIGN PATENT DOCUMENTS

| | | | |
|---|---|---|---|
| CN | 110400360 A | 11/2019 | |
| CN | 110752032 A | 2/2020 | |
| WO | WO-2014147550 A1 * | 9/2014 | ........ A61M 15/0025 |

OTHER PUBLICATIONS

Abadi, M. et al "TensorFlow: Large scale Machine Learning on Heterogeneous Distributed Systems," Google Research whitepaper, Alphabet, Mountain View, CA, USA, 2015, 19 pages.
(Continued)

*Primary Examiner* — Sheetal R Paulson
(74) *Attorney, Agent, or Firm* — Timothy H. Van Dyke; Wolter Van Dyke Davis, PLLC

(57) ABSTRACT

Techniques for artificial intelligence medicament or test delivery device sound output (MDDSO) detection includes receiving, at a neural network, processed data based on operational data that indicates a time series having a first duration for signals from a vibration detector collected during operation of a medicament device. The neural network classifies the processed data as a first MDDSO or not. The classification data is sent to an output device. The neural network has been trained, prior to receiving the operational data, with first training data and second training data. The first training data indicates time series of ambient sounds, each time series having the first duration. The second training data indicates time series of sound having the first duration during operation of the type of medicament or test
(Continued)

device, wherein each time series of the second training data includes sound from the first MDDSO emitted from the device.

19 Claims, 13 Drawing Sheets

(58) Field of Classification Search
CPC ........ G06N 3/048; G06N 3/084; G09B 23/28; A61M 5/20
See application file for complete search history.

(56) References Cited

OTHER PUBLICATIONS

Jagtap, R. "Adding Intelligent Vision to Your Next Embedded Product," ARM whitepaper. ARM Ltd, Cambridge, UK, 2019, 12 pages.

Kingma, D.P. et al., "ADAM: A Method for Stochastic Optimization," published as conference paper at International Conference on Learning Representations (ICLR) 2015, 15 pages.
Lai, L. et al., "CMSIS-NN: Efficient Neural Network Kernals for ARM Cortex-M CPUs," ARM whitepaper. ARM Ltd, Cambridge, UK, 2018, 10 pages.
Lai, L. et al., "Deep Convolutional Neural Network Inference with Floating-point Weights and Fixed-point Activations," ARM whitepaper. ARM Ltd, Cambridge, UK, 2017, 10 pages.
Shore, C. "Think Local: How to Migrate Intelligences from the Cloud to Embedded Devices at the Edge," ARM whitepaper. ARM Ltd, Cambridge, UK, 2019, 13 pages.
Suda, N. "Machine Learning on ARM Cortex-M Microcontrollers," ARM whitepaper. ARM Ltd, Cambridge, UK, 2019, 10 pages.
Zhang, Y. et al., "Hello Edge: keyword Spotting on Microcontrollers," ARM whitepaper. ARM Ltd, Cambridge, UK, 2018, 14 pages.
Zhang, Y. et al. "The Powers of Speech: Supporting Voice-Driven Commands in Small, Low-Power Microcontrollers," ARM whitepaper. ARM Ltd, Cambridge, UK, 2018, 5 pages.
PCT Search Report & Written Opinion, PCT/US2021/036580, Mailed Oct. 27, 2021, 7 pages.

* cited by examiner

100

112

MEDICAMENT
DELIVERY DEVICE (MDD)
110

190

115

MDD TRAINER 120

132      130

134

138

136

160

164

161

136

TRAINING
CORPUS 150

TRAINING SAMPLE 152

FILTERED OUTPUTS
MULTIPLE WINDOWS
154

CLASSIFICATION 156

200

INPUT LAYER 210

CONNECTIONS 212

HIDDEN LAYER 220

CONNECTIONS 223

HIDDEN LAYER 230

HIDDEN LAYER 240

CONNECTIONS 245

OUTPUT LAYER 250

RECTIFIED LINEAR UNITS
(ReLU)

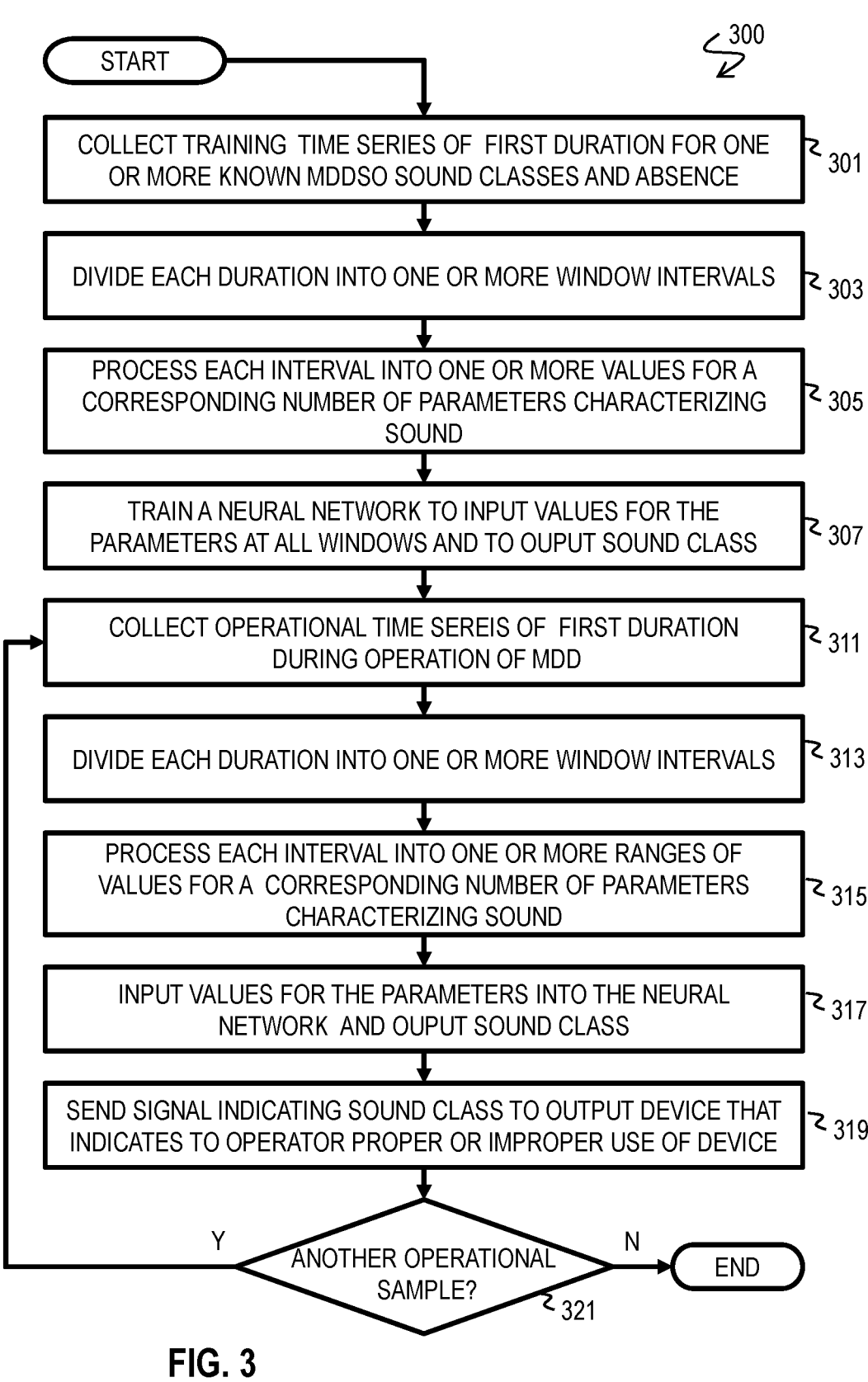

START

COLLECT TRAINING TIME SERIES OF FIRST DURATION FOR ONE OR MORE KNOWN MDDSO SOUND CLASSES AND ABSENCE — 301

DIVIDE EACH DURATION INTO ONE OR MORE WINDOW INTERVALS — 303

PROCESS EACH INTERVAL INTO ONE OR MORE VALUES FOR A CORRESPONDING NUMBER OF PARAMETERS CHARACTERIZING SOUND — 305

TRAIN A NEURAL NETWORK TO INPUT VALUES FOR THE PARAMETERS AT ALL WINDOWS AND TO OUPUT SOUND CLASS — 307

COLLECT OPERATIONAL TIME SEREIS OF FIRST DURATION DURING OPERATION OF MDD — 311

DIVIDE EACH DURATION INTO ONE OR MORE WINDOW INTERVALS — 313

PROCESS EACH INTERVAL INTO ONE OR MORE RANGES OF VALUES FOR A CORRESPONDING NUMBER OF PARAMETERS CHARACTERIZING SOUND — 315

INPUT VALUES FOR THE PARAMETERS INTO THE NEURAL NETWORK AND OUPUT SOUND CLASS — 317

SEND SIGNAL INDICATING SOUND CLASS TO OUTPUT DEVICE THAT INDICATES TO OPERATOR PROPER OR IMPROPER USE OF DEVICE — 319

Y    ANOTHER OPERATIONAL SAMPLE?    N    END
— 321

ARTIFICIAL INTELLIGENCE FOR SOUND DETECTION FROM MEDICAMENT OR TEST DEVICE

BACKGROUND

Performing a medical treatment or test on oneself carries with it certain risks, and often creates a level of anxiety for the user performing the treatment or test. It has proven beneficial in the medical field to practice various medical techniques including drug delivery, specifically where it relates to injections and other invasive drug delivery means prior to delivering the medications to a patient in need, and particularly in the case of self-administration of medicaments. Training devices are helpful in reducing errors and anxiety associated with self-administering medical treatment, as well as increasing efficiency and accuracy in providing the treatment to patients. Medical devices can be intimidating to use; the fear associated with giving oneself an injection, for example, can be traumatic. This fear is increased in persons with little or no experience in self-administration of medications. Consequently, training devices and methods to assist in training individuals to inject themselves or otherwise self-administer medication are beneficial in decreasing or preventing the anxiety associated with medicament delivery. Medicament delivery training devices allow patients to practice giving themselves a full dose in a safe and effective manner.

SUMMARY

Techniques are provided for artificial intelligence detection of medicament or test delivery device sound output (MDDSO), either alone or in conjunction with a training device therefor. The character and timing of such MDDSOs are indicative of proper or improper use of the delivery device.

In a first set of embodiments, a method for artificial intelligence medicament or test delivery device sound output (MDDSO) detection includes receiving, at a processor configured as a neural network, operational data that indicates a time series having a duration of at least a first duration for signals from a vibration detector collected during operation of an instance of a type of medicament device. The method also includes generating automatically, on the neural network, classification data that classifies the operational data as a first MDDSO or not by inputting processed data based on the operational data into an input layer of the neural network. Still further, the method includes sending the classification data as a signal to an output device. The neural network has been trained, prior to receiving the operational data, with first training data and second training data. The first training data indicates a plurality of time series of ambient sounds, each time series having the first duration. The second training data indicates a plurality of time series of sound having the first duration during operation of the type of medicament device, wherein each time series of the second training data includes sound from the first MDDSO emitted from the medicament device.

In some embodiments of the first set, prior to receiving the operational data, the neural network has been trained further with third training data that indicates a plurality of time series of sound having the first duration during operation of the type of medicament device. Each time series of the third training data includes sound from a different second MDDSO emitted from the medicament device, wherein the second MDDSO follows in time the first MDDSO during normal operation of the type of medicament device. The classification data further classifies the operational data as the first MDDSO or the second MDDSO or neither.

In some of these latter embodiments of the first set, prior to receiving the operational data, the neural network has been trained further with fourth training data that indicates a plurality of time series of sound having the first duration during operation of the type of medicament device. Each time series of the fourth training data includes sound from a different third MDDSO emitted from the medicament device, wherein the third MDDSO follows in time the first MDDSO during normal operation of the type of medicament device. The classification data further classifies the operational data as the first MDDSO or the second MDDSO or the third MDDSO or none.

In some embodiments of the first set, the operational data and the training data time series are each divided into one or more window time intervals, and a value for a certain parameter characterizing the sound in each window time interval is used as an input value for each node of an input layer of the neural network.

In some embodiments with one or more window time intervals, the certain parameter characterizing the sound in each time interval is a power spectrum value for a particular frequency interval. In some of these embodiments, the power spectrum value for a particular frequency interval involves multiple power spectrum values for a corresponding multiple frequency intervals. In some of these embodiments, the multiple frequency intervals include a number of frequency intervals in a range from about 2 to about 40 frequency intervals. In some of these embodiments the MDDSO is a click; and, the multiple frequency intervals span a frequency range from about 0 Hertz to about 4 kilohertz.

In some embodiments with one or more window time intervals, the certain parameter characterizing the sound in each time interval is a value for a particular cepstral coefficient interval. In some of these embodiments, the value for a particular cepstral coefficient interval involves multiple values for a corresponding multiple cepstral coefficient intervals. In some of these embodiments, the plurality of cepstral coefficient intervals comprises a number of cepstral coefficient intervals in a range from about 2 to about 40 cepstral coefficient intervals. In some of these embodiments, the MDDSO is a click; and, the multiple cepstral coefficient intervals span a cepstral coefficient range from about 0 to about 12.

In some embodiments with one or more window time intervals, the certain parameter characterizing the sound in each time interval is a value output by a particular filter. In some of these embodiments, the value output by the particular filter involves multiple values output by a corresponding multiple filters. In some of these embodiments, the multiple filters include about 10 to about 60 filters; or, alternatively, about 20 to about 40 filters.

In some embodiments of the first set, the first duration is selected in a range from about 10 milliseconds to about 2000 milliseconds.

In some embodiments with one or more window time intervals, the first duration is selected in a range from about 10 milliseconds to about 2000 milliseconds and each window time interval is selected in a range from about 10 milliseconds to about 130 milliseconds. Also, the window time interval is less than or equal to the first duration.

In some embodiments of the first set, the neural network includes a number of hidden layers of nodes selected in a range from 1 to about 5 hidden layers.

In some embodiments of the first set, the neural network includes at least one convolutional hidden layer. In some of these embodiments, the neural network includes at least one fully connected hidden layer.

In some embodiments of the first set, the neural network includes multiple depth-wise separable convolutional hidden layers.

In some embodiments of the first set, the neural network includes a long, short-term-memory network.

In other sets of embodiments, a non-transient computer-readable medium, or an apparatus, or a neural network, or system is configured to perform one or more steps of the above methods.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 3 is a flow diagram that illustrates an example method to train and utilize a neural network for classifying MDDSO, according to an embodiment;

FIG. 4C is an annotated plot that illustrates example acoustic data and example first duration and window time intervals, according to various embodiments;

FIG. 4D is a block diagram that illustrates example frequency interval processed data for input to a neural network, according to an embodiment;

FIG. 4E is a block diagram that illustrates example cepstral coefficient interval processed data for input to a neural network, according to another embodiment;

FIG. 5A through FIG. 5C are annotated photographs that illustrate example components of a medicament delivery device trainer apparatus, according to an experimental embodiment

DETAILED DESCRIPTION

A method and apparatus and system are described for artificial intelligence detection of medicament delivery device sound output (MDDSO), either alone or in conjunction with a training device therefor. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus, a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5x to 2x, for example, about 100 implies a value in a range from 50 to 200. Moreover, all ranges disclosed herein are to be understood to encompass any and all sub-ranges subsumed therein. For example, a range of "less than 10" for a positive only parameter can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of detecting clicks from an injection delivery device and associated trainer. However, the invention is not limited to this context. In other embodiments, other sounds are detected and classified from the same or different medicament delivery or testing devices, with or without their respective training devices, for determining correct operation or for other purposes.

1. OVERVIEW

Figure 1A:
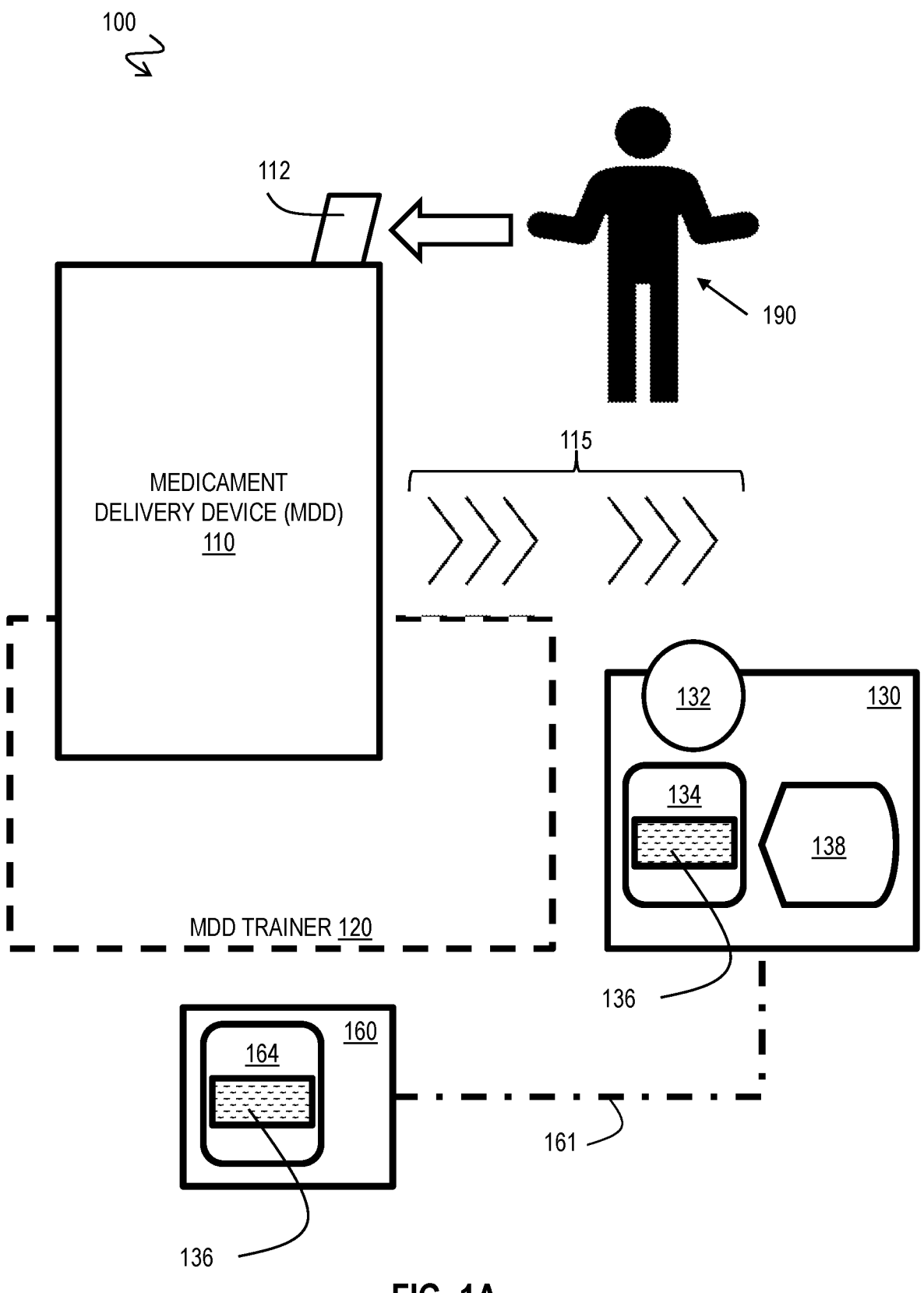
FIG. 1A is a block diagram that illustrates an example system for artificial intelligence detection of medicament delivery device sound output (MDDSO), according to an embodiment.

FIG. 1A is a block diagram that illustrates an example system 100 for artificial intelligence detection of medicament delivery or testing device sound output (MDDSO), according to an embodiment. Although a human operator 190 is depicted for purposes of illustration, the human operator 190 is not part of the system 100. The human operator 190, in various embodiments, is a medical care giver undergoing training for administering a medicament or test to a human or animal patient, or a medical care giver administering a medicament or test to a human or animal patient in a clinical setting, or a human patient undergoing training, or a human patient during self-administration of a medicament or test.

The system includes a medicament or test delivery device (MDD) 110, such as an intravenous hypodermic needle with plunger, a subcutaneous needle and plunger, a needle array, a applicator for a device to be attached above or below a skin of the patient (e.g., a continuous glucose monitor), or any of a number of known or still developing medical treatment or monitoring devices. The MDD includes at least one operational component 112 to be manually operated by the operator 190 in a sequence of one or more manual actions by the operator 190. Examples of component 112 include a plunger, a button, a dial, a removeable tab, a switch, or some other known or still developing human interface. During operation of the component 112 of the MDD 110, one or more distinct or continuous sounds, or some combination, each called herein an MDD sound output (MDDDSO), is emitted; and represented in FIG. 1 as acoustic wave fronts 115.

The system 100 also includes an artificial intelligence (AI) MDDSO detector 130. The AI MDDSO detector 130 includes a vibration sensor 132 such as a microphone sensitive in at least a portion of the audible range, e.g., 40 Hertz (Hz) to 40 kilohertz (kHz, 1 kHz=$10^3$ Hz). Vibrations in solids, liquids, or gasses at, or below, or above the audible range, or some combination, are also used in various embodiments. Thus, in some embodiments the vibration sensor 132 is, replaces, or augments a microphone. The AI MDDSO detector 130 also includes a classification module 134 that processes a time series of acoustic data collected by vibration sensor 132 during each sampling time interval to a form of processed data that can be input to neural network 136. The output of neural network 136 is a classification for the MDDSO during each sampling time interval. Data indicating that classification is sent in a signal to an output device, such as display 138, or to an optional training device (e.g., MDD trainer 120). The signal can be an audio signal such as a tone or melody or spoken message (indicating approval or the error made or instructions for use, IFU, or some remedial action). The signal can be a video signal such as a colored light (e.g., red for improper operation or green for proper operation, with intervening colors for other conditions), an emoji, an animated cartoon or prerecorded video clip (indicating approval or the error made or IFU, or some remedial action). In some embodiments the signal indicates a classification of a single MDSSO. In some embodiments the signal indicates a correct sequence of the MDSSOs.

Figure 6:
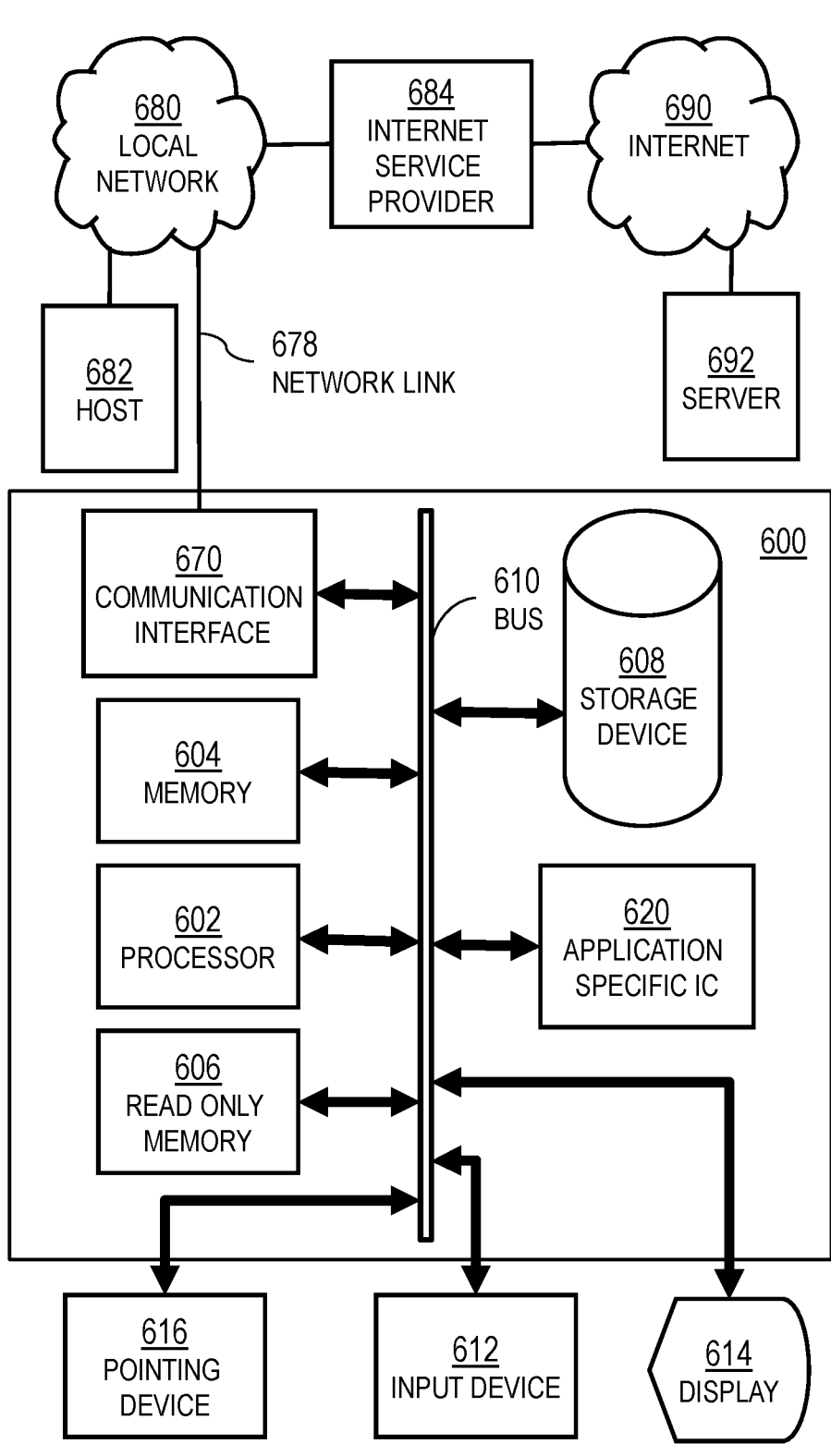
FIG. 6 is a block diagram that illustrates a computer system upon which an embodiment of the invention may be implemented.
Figure 7:
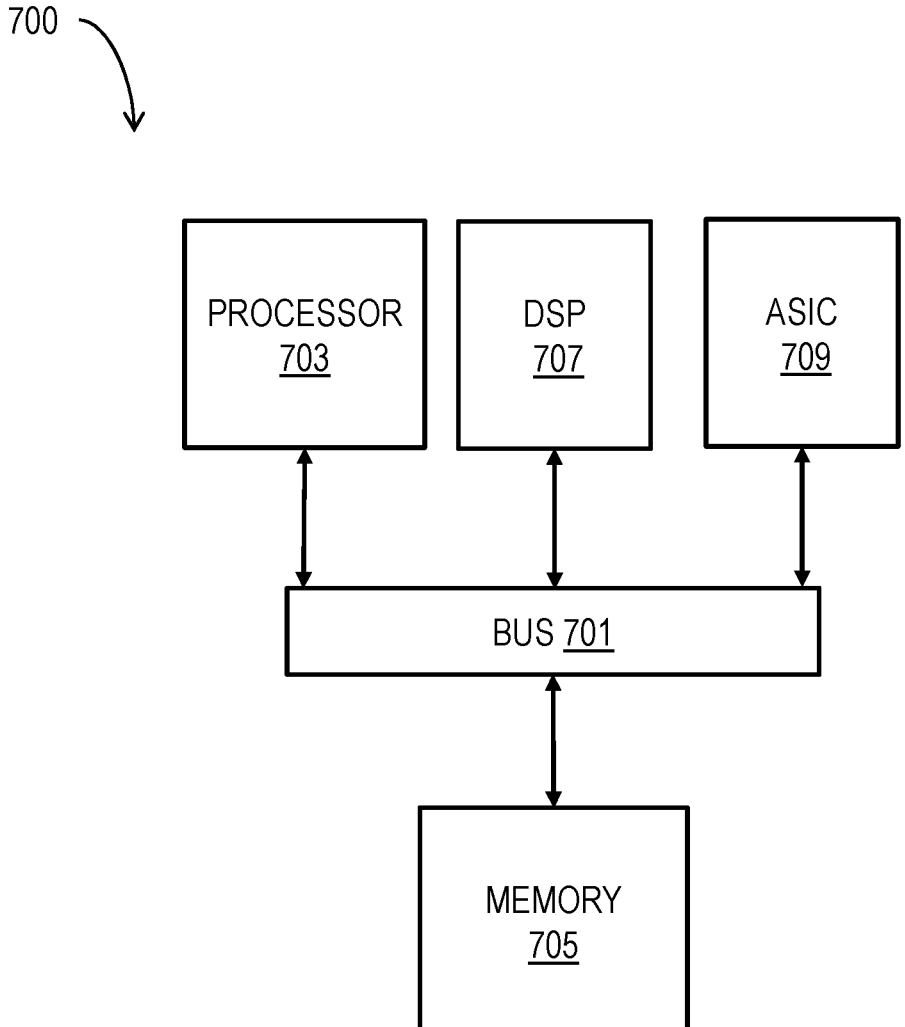
FIG. 7 illustrates a chip set upon which an embodiment of the invention may be implemented.
Figure 8:
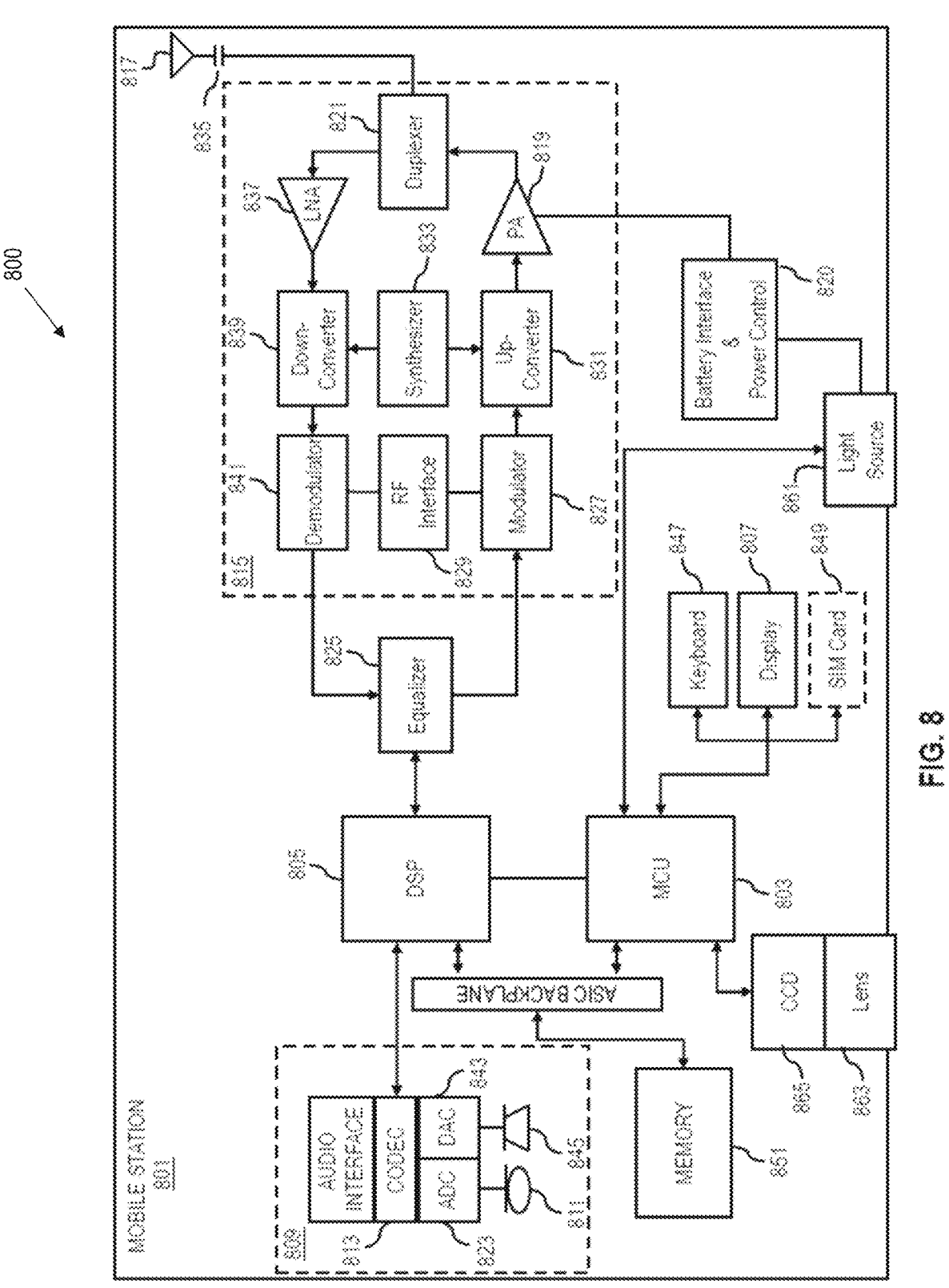
FIG. 8 is a diagram of example components of a mobile terminal (e.g., cell phone handset) for communications, which is capable of operating in the system, according to one embodiment.

In various embodiments, the classification module 134 is implemented, in whole or in part, in a chip set 700 as depicted in FIG. 7, or an application specific integrated circuit (ASIC), e.g., ASIC 620 in a separate computer system 600 depicted in FIG. 6, or a headphone jack or universal serial bus (USB) or power port attachment to a mobile communications device, such as mobile terminal 800 depicted in FIG. 8. In some embodiments, all or part of classification module 134, including neural network 136, is implemented as module 164 on a remote server 160 and communicated to a local device 130 having a vibration sensor 132, display 138, and some processing power to process or pre-process the acoustic data, e.g., mobile terminal 800 with microphone 811 and video display 807 or audio output speaker 845, via a wired or wireless communications link 161, including any local or global network.

In some embodiments, the system 100 also includes optional MDD training device, also called MDD trainer 120. The MDD trainer 120 is configured to provide appropriate feedback to the operator, e.g., in terms of resistance pressure; or, configured to measure the amount of medicament delivered; or, to detect proper forces and sequence of the operation of component 112; or some combination; or to display a result, such as pass or fail.

In some embodiments, the MDDSO detector 130 is incorporated into the MDD trainer 120, e.g., instead of in a separate device, such as mobile communications terminal 800. Incorporating the MDDSO detector 130 into the trainer is advantageous because then a single device can be used during training, and the result displayed by the trainer can be based, at least in part, on the signal output by the detector 130. In such embodiments, any display included in trainer 120 can be used in lieu of display 138; and, display 138 can be omitted. Often the need for the MDDSO detection is reduced after proper training; and, the use of the MDDSO detector 130 is optionally omitted during clinical use of the MDD 110.

In general, it is not expected that an AI system will be able to characterize a sound when the acoustic time series collected during a sampling interval is reduced to a single value. Nor is it practical or expected to be necessary to include every acoustic pressure sample on the sub-millisecond scale to properly characterize the sound. Thus, in general, the acoustic time series is reduced to a discrete set of inputs that characterize the sound collected using one or more parameters of sound, e.g., by characterizing the total energy in each of multiple different time window intervals within the sample duration, or by the amplitudes of various frequency bands in the sample duration or sub-intervals of the sample duration, or other parameters described below. A limited number of discrete input values is advantageous for the use of neural networks in an AI system. In various embodiments, for typical MDDSO, the sample duration is selected in a range from about 10 milliseconds (ms, 1 ms=$10^{-3}$ seconds) to 2000 ms.

Although processes, equipment, and data structures are depicted in FIG. 1A as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts. For example, in some embodiments, detector 130 is incorporated into trainer 120.

Figure 1B:
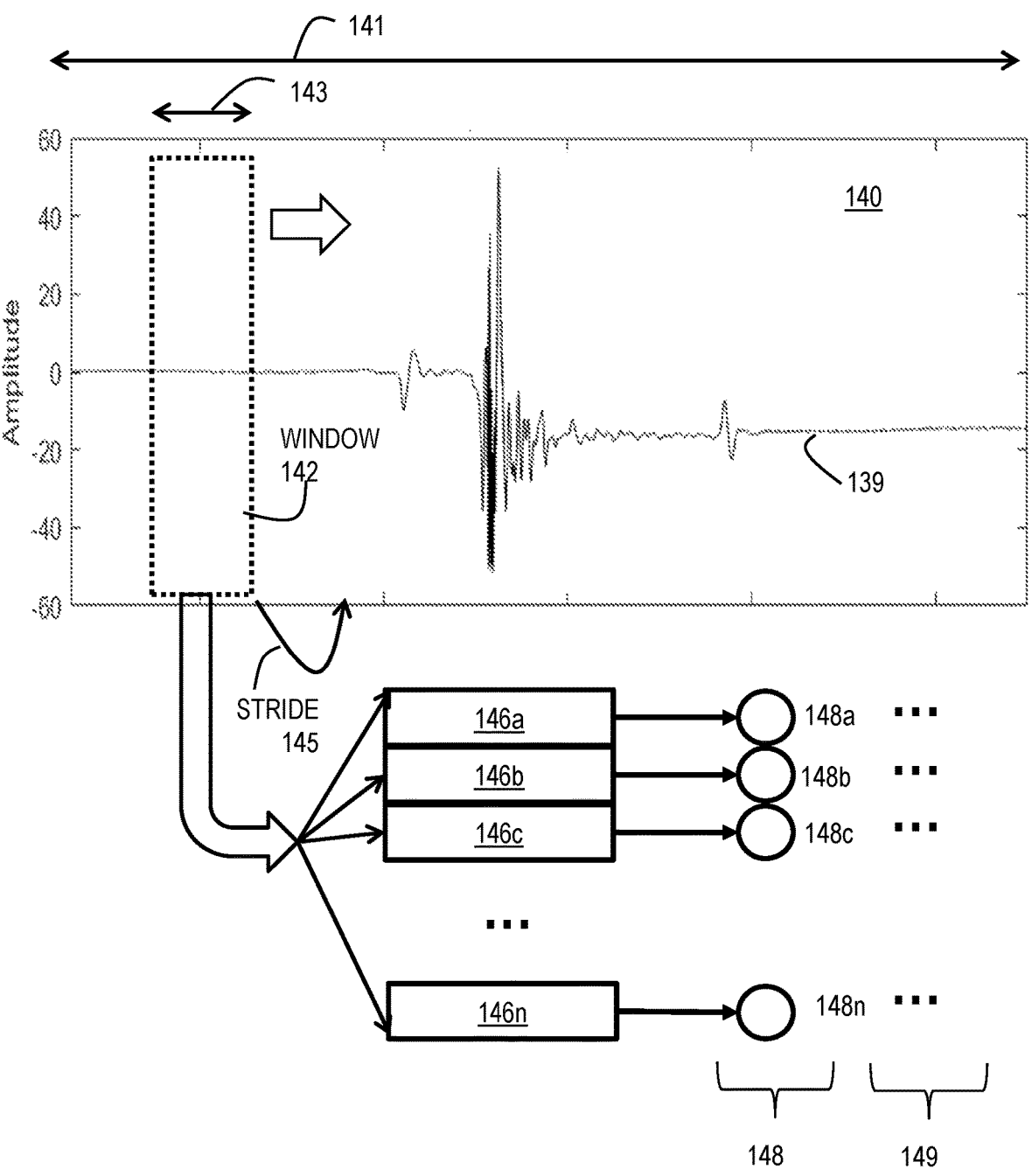
FIG. 1B is a block diagram that illustrates an example system for processing vibration data from a medicament delivery device for input to a neural network, according to an embodiment.

FIG. 1B is a block diagram that illustrates an example system for processing acoustic data from a medicament or test delivery device for input to a neural network, according to an embodiment. Full resolution acoustic data collected by sensor 132 over duration is represented by trace 139 on plot 140 over a time duration 141. The horizontal axis of plot 140 indicates time in arbitrary units representing many hundreds of milliseconds. The vertical axis indicates amplitude of the acoustic pressure in arbitrary units relative to a reference pressure such as atmospheric pressure.

The sample duration 141 is divided into one or more time windows 142, each having a time interval 143. The sound in window 142 is fed into one or more filters 146, such as filter

146a, 146b, among others indicated by ellipsis, through filter 146n. Each filter produces a single value that is based on the sound in window 142, e.g., the value for a certain parameter characterizing the sound. In various embodiments the filters 146 include components that convert the time series in the window 142 into another time series that is subsequently characterized by values for one or more parameters. Such components include, in various embodiments analog or digital, all-pole filters, multi-pole filters, single pole filters, triangular band pass filters. Some filters with increased width at high frequencies operating on a Fourier transform power spectrum produce a Mel-scale spectrum intended to align with human hearing. The values output by filters 146 are processed data. The processed values produced by filters 146 are used as input to the neural network as described in more detail below. For example, the processed values produced by filters 146a, 146b, 146c through 146n are placed, respectively, into input nodes 148a, 148b, 148c, through 148n (collectively referenced as input nodes 148) of a neural network. Thus, the certain parameter characterizing the sound in each time interval is a value output by a particular filter or a plurality of values output by a corresponding plurality of filters. In various embodiments there are about 10 to about 60 filters, or about 20 to about 40 filters.

In embodiments with more than one window 142 per sampling duration (e.g., when window time interval 143 is less than sample duration 141), additional processed values are produced by each filter during other windows, and input to other neural network input nodes 149 represented by ellipses to the right of nodes 148 in FIG. 1B. The separation in time of adjacent windows is given by stride 145. In embodiments with contiguous non-overlapping windows, stride 145 is equal to time interval 143; but, in various other embodiments overlapping windows with stride shorter than time interval 143, and non-contiguous windows with stride 145 larger than time interval 143 are used.

Any implementation of filters to provide values of any parameter characterizing sound in a window may be used, including analog or digital implementations or some combination. In various embodiments, the parameters are for any statistic that characterizes the sound in a window (number of peaks, peak value, mean, variance, skew, kurtosis, frequency band energy density, etc.). Frequency band energy is typically computed using a Fourier transform of the acoustic trace 139 of the portion thereof in window 142. In some embodiments cepstral coefficients are used to characterize the sound in a window. A cepstral coefficient is a reverse Fourier or cosine or similar transform of a logarithm of the spectral amplitudes produced by the corresponding forward transform from the time domain to the frequency domain. Cepstral coefficients serve as tools to investigate periodic structures within frequency spectra. The energy in a particular band of cepstral coefficients is used in some embodiments as the parameter; and is thus output by one or more of filters 146.

Figure 1C:
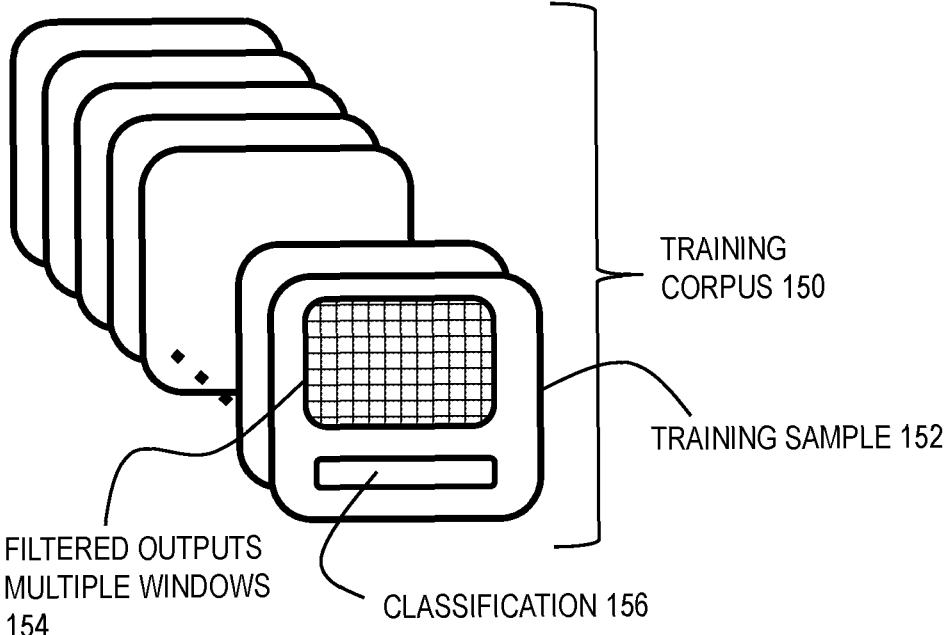
FIG. 1C is a block diagram that illustrates an example training set of processed vibration data and classifications to program the neural network, according to an embodiment.

Associated with each sample interval is zero or more MDDSO that an expert would be able to ascertain. It is a characteristic of an AI system that a particular result is learned for a particular input, and this involves a training set (also called a training corpus) in which both the inputs are provided and the correct result is known, i.e., the output is also given. The AI system then configures itself to produce that proper output given the input. In order to prevent the system from relying on random accidental associations, the training set is advantageously large with a wide variety of normal variations that still provide each of several desired outputs. FIG. 1C is a block diagram that illustrates an example training set 150 of processed acoustic data and MDDSO classifications to program the AI neural network, according to an embodiment. For each training sample 152 in the training corpus 150 there is a set 154 of one or more filtered outputs for each of one or more window intervals. Also included in training sample 152 is a correct MDDSO classification 156, including the absence of any MDDSO, e.g., determined by an expert or by a controlled experiment.

Figure 2A:
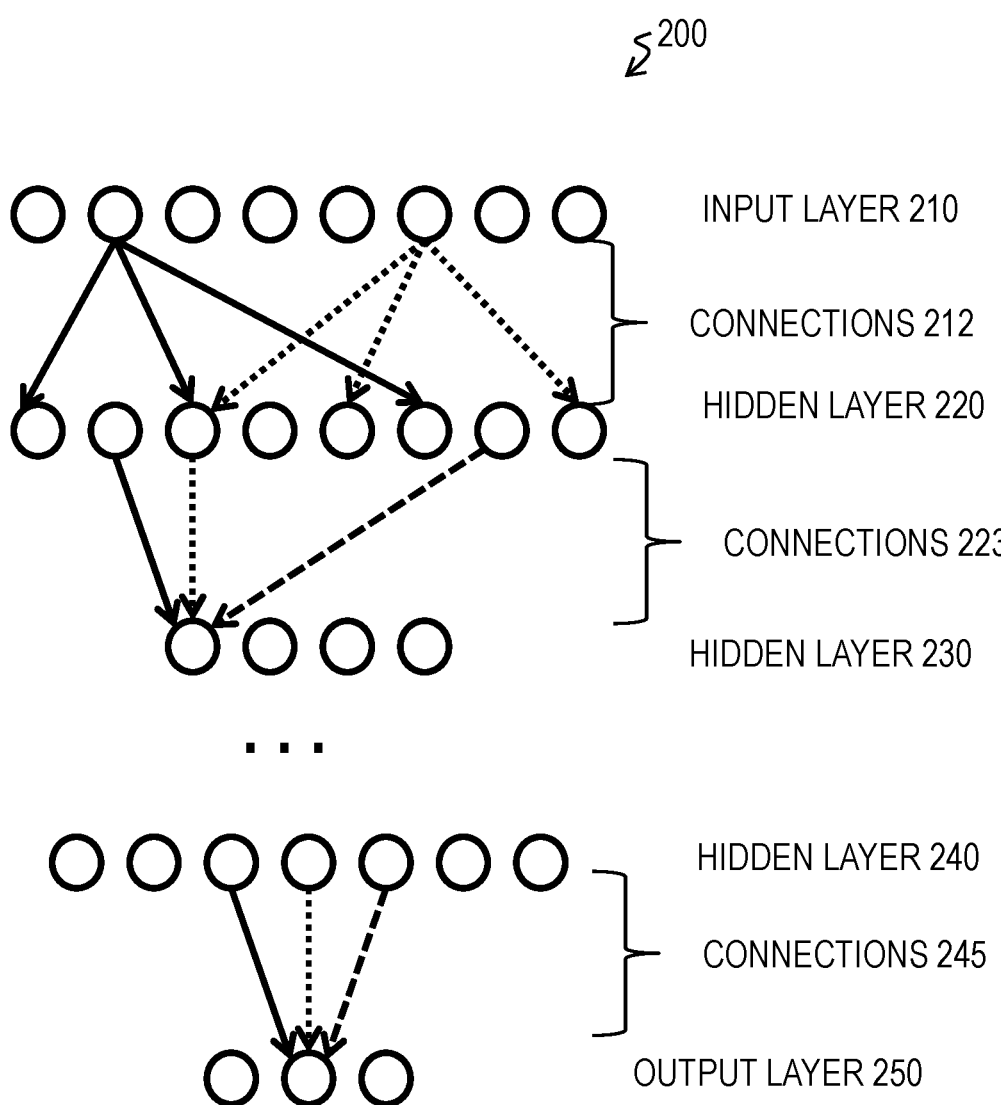
FIG. 2A is a block diagram that illustrates an example neural network for classifying processed vibration data, according to an embodiment.

Effective training of an artificial intelligence system with the characteristics described above can be achieved using neural networks, widely used in image processing and textual natural language processing. FIG. 2A is a block diagram that illustrates an example neural network 200 for illustration. A neural network 200 is a computational system, implemented on a general-purpose computer, or field programmable gate array, or some application specific integrated circuit (ASIC), or some neural network development platform, or specific neural network hardware, or some combination. The neural network is made up of an input layer 210 of nodes, at least one hidden layer 220, 230 or 240 of nodes, and an output layer 250 of one or more nodes. Each node is an element, such as a bit or register or memory location, that holds data that indicates a value. The value can be code, binary, integer, floating point or any other means of representing data. Values in nodes in each successive layer after the input layer in the direction toward the output layer is based on the values of one or more nodes in the previous layer. The nodes in one layer that contribute to the next layer are said to be connected to the node in the later layer. Connections 212, 223, 245 are depicted in FIG. 2A as arrows. The values of the connected nodes are combined at the node in the later layer using some activation function with scale and bias (also called weights) that can be different for each connection. Neural networks are so named because they are modeled after the way neuron cells are connected in biological systems. A fully connected neural network layer has every node at the layer connected to every node at the next layer.

Figure 2B:
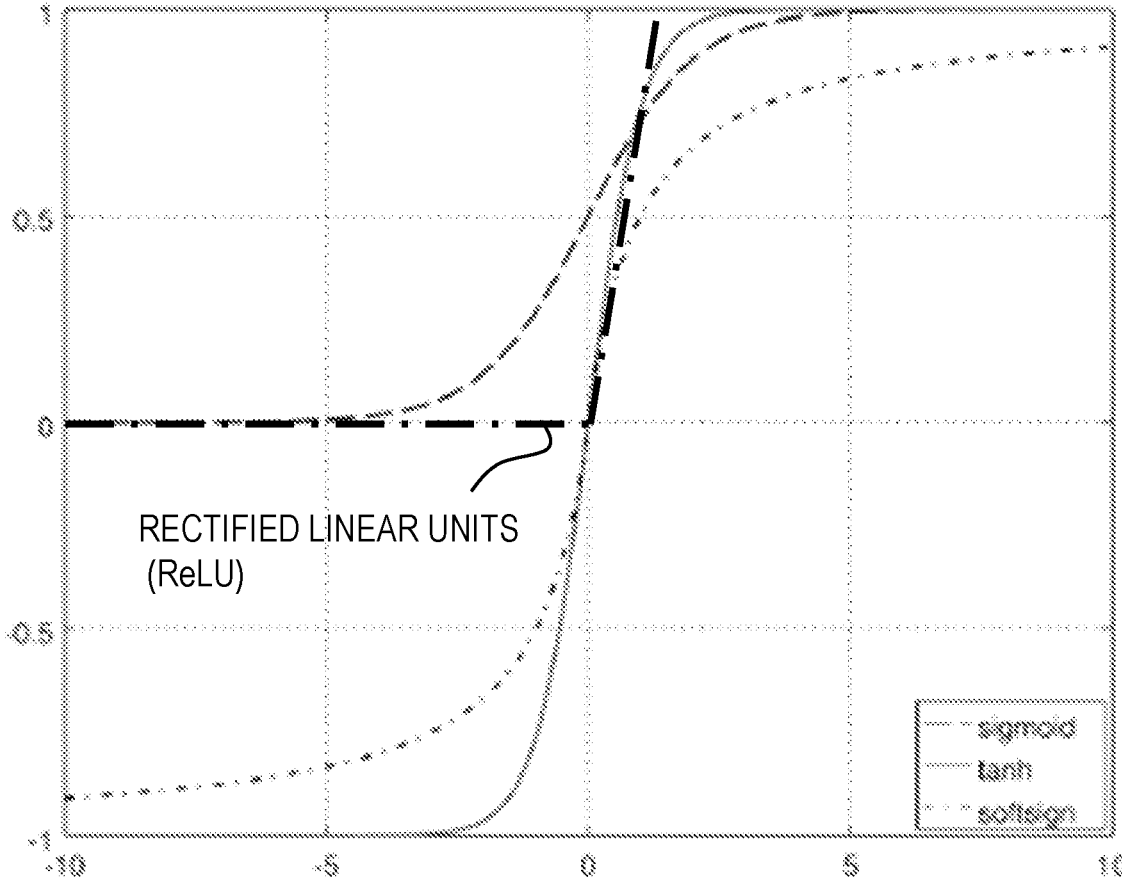
FIG. 2B is a plot that illustrates example activation functions used to combine inputs at any node of a feed forward neural network, according to various embodiments.

FIG. 2B is a plot that illustrates example activation functions used to combine or modify inputs at any node of a neural network. These activation functions are normalized to have a magnitude of 1 and a bias of zero; but when associated with any connection can have a variable magnitude given by a weight and centered on a different value given by a bias. The values in the output layer 250 depend on the values in the input layer, any function combination of those inputs (such as a sum or multiplication) and the activation functions used at each node and the weights and biases associated with each connection that terminates on that node. The sigmoid activation function (dashed trace) has the properties that values much less than the center value do not contribute to the combination (a so-called switch off effect) and large values do not contribute more than some maximum value to the combination (a so-called saturation effect), both properties frequently observed in natural neurons. The tanh activation function (solid trace) has similar properties but allows both positive and negative contributions. The softsign activation function (short dash-dot trace) is similar to the tanh function but has much more gradual switch and saturation responses. The rectified linear units (ReLU) activation function (long dash-dot trace) simply ignores negative contributions from nodes on the previous layer, but increases linearly with positive contributions from the nodes on the previous layer; thus, ReLU activation exhibits switching but does not exhibit saturation. In some embodiments, the activation function operates on individual connections before a subsequent operation, such as summation or multiplication; in other embodiments, the activation function operates on the sum or product of the values in the connected nodes. In other embodiments, other activation functions or combinatorial functions are used, such as kernel convolution.

An advantage of neural networks is that they can be trained to produce a desired output from a given input without knowledge of how the desired output is computed. There are various algorithms known in the art to train the neural network on example inputs with known outputs. Typically, the activation function for each node or layer of nodes is predetermined, and the training determines the weights and biases for each connection. A trained network that provides useful results, e.g., with demonstrated good performance for known results, is then used in operation on new input data not used to train or validate the network.

In some neural networks, the activation functions, weights and biases, are shared for an entire layer. This provides the networks with shift and rotation invariant responses. The hidden layers can also consist of convolutional layers, pooling layers, fully connected layers and normalization layers. The convolutional layer has parameters made up of a set of learnable filters (or kernels), which have a small receptive field. In a pooling layer, the activation functions perform a form of non-linear down-sampling, e.g., producing one node with a single value to represent several nodes (e.g., four nodes) in a previous layer. There are several non-linear functions to implement pooling among which max pooling is the most common. A normalization layer simply rescales the values in a layer to lie between a predetermined minimum value and maximum value, e.g., 0 and 1, respectively.

A convolution neural network (CNN) layer, with each node having a limited view of the previous layer and a convolution (sum of dot products) kernel, but all nodes having the same limited view and kernel, has been useful in visual object recognition when the object can be randomly placed and oriented in a field of view. Here that property is used, in some embodiments, to identify a MDDSO (e.g., large oscillations in trace 139) in any window 142 within a sample duration 141.

A depth-wise separable convolutional (DS-CNN) hidden layer has fewer parameters to adjust as compared to the standard CNNs, which reduces overfitting and provides better accuracy. DS-CNNs are computationally cheaper because of fewer computations which makes them suitable for mobile vision applications.

Long short-term memory (LSTM) is an artificial recurrent neural network (RNN) architecture used in the field of deep learning. Unlike standard feedforward neural networks, diagrammed in FIG. 2A, LSTM has feedback connections. An LSTM can not only process single time data (such as images), but also entire sequences of data (such as speech or video). For example, LSTM is applicable to tasks such as unsegmented, connected handwriting recognition, speech recognition and anomaly detection in network traffic or intrusion detection systems.

In various embodiments one or more hidden layers include a CNN, a DS-CNN, a LSTM NN or some combination among multiple hidden layers. In an example embodiment, the input layer and the output layer are each fully connected to the adjacent hidden layer. In various embodiments, 1 to 5 hidden layers are included. In an experimental embodiment, 3 hidden layers are used.

2. METHOD

FIG. 3 is a flow diagram that illustrates an example method 300 to train and utilize a neural network for classifying MDDSO, according to an embodiment. Although steps are depicted in FIG. 3 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 301, multiple training time series of acoustic sensor data of at least a first duration are collected, e.g., from vibration sensor 132, for each of one or more known MDDSO classes and one or more absences thereof. Associated with each time series is a sound classification indicating one of the one or more MDDSO classes or absences. For example, 1000 time series are collected for each of one, two or three or more MDDSO classes and one or more classes with MDDSO absent. Thus, in some embodiments, the classification data classifies the operational data as the first MDDSO or the second MDDSO or the third MDDSO or other or none of one or more absence types. Examples of classes with MDDSO absent are: durations of silence, or with ambient sounds not including any of the MDDSO classes under one or more conditions, such as rustling of papers and chairs with a single person in a room, conversations of two or more persons in a room, fans or air conditioning equipment humming in a room. Examples of MDDSO classes includes first or second clicks of a hypodermic needle plunger, start or one or more middle intervals or end, or some combination, to whirring of an activated motor, beginning or middle or end of, or some combination, a swoosh of insertion of subcutaneous wire or sensor, start or middle or end of, or some combination, a slap of a patch of microneedles, initial or one or more partial or complete dispensing, or some combination, from a nasal pump, among others. In some embodiments, an MDDSO is an activation sound from the medicament or test device, which sound indicates primary operation of the type of medicament or test device. One or more such sounds are emitted from one or more of the following devices: needle shield release; plunger movement in a pre-filled syringe; button activation on an inhaler; medicament dispersion in an inhaler; manual device settings on a multi-dose injector (dial-dose); sounds associated with device shaking; needle attachment twist-lock mechanisms, nasal devices including nasal pumps, and plastic/plastic contact not associated with the needle plunger such as needle shield interaction or button press. In some embodiments, an MDDSO is a non-activation sound from the medicament or test device (e.g., cap removal, device reset), which sound does not indicate primary operation of the type of medicament or test device. In some embodiments an MDDSO is a sound from a different type of medicament or test device (e.g., different auto-injector platforms, an inhaler versus an injector, the medicament device itself as distinguished from a trainer for the medicament device).

The first duration is determined for the training time series. In various embodiments, any duration suitable for the sound class to be detected may be used. For example, in detecting clicks with a time scale of a few milliseconds, a first duration of ten milliseconds to about one second is suitable. For sounds with somewhat longer time scales such as one second, a first duration of up to 2 seconds (2000 milliseconds) or more is suitable. Longer time series can be truncated at the beginning or end or both. In various embodiments, the first duration is selected in a range from 10 ms to 2000 ms, or in a subrange, such as 20 ms to 2000 ms, or 50 ms to 2000 ms, or 100 ms to 2000 ms, or 10 ms to 1000 ms, or 100 ms to 1000 ms, or 50 ms to 1000 ms, or 50 ms to 500 ms, or 100 ms to 500 ms.

In step 303 each time series, truncated as needed to the first duration, is divided into one or more, contiguous or non-contiguous, overlapping or non-overlapping, window time intervals. In various embodiments, the window time interval is selected to generate a number of window time intervals in a range from 1 to 100 intervals, or 1 to 10 intervals, or 2 to 8 intervals, or 4 to 8 intervals. Thus, the window time intervals are selected to be in a range from 10 ms to 200 ms, or 10 ms to 150 ms, or 10 ms to 130 ms, or 10 ms to 100 ms, or 50 ms to 100 ms.

In step 305, acoustic time series data in each window time interval is processed, e.g., in one or more filters 146, to produce corresponding one or more values for a corresponding number of parameters characterizing the sound in the window. Each filter produces one value for one parameter, such as energy in a particular frequency range or a particular cepstral coefficient range. In some embodiments, some filters produce energy value for a frequency range and other filters produce energy values in a particular cepstral coefficient range, so various filters can be mixed across different types of parameters. Values for various parameters can be produced in various embodiments, as described above. For example, in some embodiments, the certain parameter characterizing the sound in each window time interval is a power spectrum value for a particular frequency interval or a plurality of power spectrum values for a corresponding plurality of frequency intervals. In some embodiments, the certain parameter characterizing the sound in each window time interval is a value for a particular cepstral coefficient interval or a plurality of values for a corresponding plurality of cepstral coefficient intervals. The result of step 305 is the training set 150 depicted in FIG. 1C.

In step 307, the neural network 136 is trained to produce the correct classification as output for the values of the processed data provided at the input nodes. The neural network has an input layer with a node for each value of the processed data. In some embodiments, each input node represents a range bin of values for a single parameter and the input node can be binary (the parameter value falls in that range or not). In other embodiments, the input nodes hold values that represent an amplitude for a particular statistic or frequency band; and, the node holds a floating-point number in a floating-point register or a normalized integer in an integer register. The value at the output layer can be expressed in any manner known. For example, in some embodiments, each node in the output layer represents a different class; and the output node representing the classification result has a value of one and the remaining output values have a value of zero. Thus, the output layer can be binary in some embodiments. In other embodiments, values in the output nodes indicate the probability for the corresponding classification, so the output nodes are floating-point registers or normalized integers.

Thus, in step 307, the neural network is trained with first training data that indicates a plurality of time series of ambient sounds, each time series having the first duration, and with second training data that indicates a plurality of time series of sound having the first duration during operation of the type of medicament or test device. Each time series of the second training data includes sound from the first MDDSO emitted from the medicament device. If there is more than one type of MDDSO or more than one type of absence of MDDSO, the same neural network is subjected to training sets for those classes as well. Thus, in some embodiments, in step 307, the neural network has been trained further with third training data that indicates a plurality of time series of sound having the first duration during operation of the type of medicament device, wherein each time series of the third training data includes sound from a different second MDDSO emitted from the medicament device, wherein the second MDDSO follows in time the first MDDSO during normal operation of the type of medicament device. And in some embodiments, during step 307, the neural network has been trained further with fourth training data that indicates a plurality of time series of sound having the first duration during operation of the type of medicament device, wherein each time series of the fourth training data includes sound from a different third MDDSO emitted from the medicament device, wherein the third MDDSO follows in time the first MDDSO during normal operation of the type of medicament device.

Any neural network architecture may be used for neural network 136, such as one to five hidden layers involving zero or more fully-connected, CNN, DS-CNN, LSTM, or pooling layers. Thus, in various embodiments, the neural network comprises a number of hidden layers of nodes selected in a range from 1 to about 5 hidden layers, or the neural network comprises at least one convolutional hidden layer, or the neural network comprises at least one fully connected hidden layer, or the neural network comprises a long, short-term memory network, or some combination.

Any training appropriate for the type of neural network may be used. Any neural network platform may be used to build and train the neural network 136

In step 311, one time series of vibration data of at least the first duration, called an operational time series, is collected by vibration sensor 132 during operation of the MDD by an operator 190, in the context of a patient training or clinical situation, with or without the trainer 120. In some embodiments, several different neural networks are configured to recognize sounds from different types of devices. In some of these embodiments, step 311 includes receiving information indicating the type of medicament or test device, such as receiving input indicating the type of device to be operated, or using an image capture device, such as a cell phone camera to identify the type of device being used. Then, step 311 retrieves configuration data that indicates configuration of the neural network for the type of medicament or test device just identified. Further, the processor is configured based on the configuration data as the neural network for the type of medicament or test device.

In step 313, the one operational time series is divided into one or more window time intervals consistent with the way the multiple training time series were divided into window time intervals. In step 315, the one operational time series data in each window time interval is processed, e.g., in one or more filters 146, to produce a corresponding one or more values for a corresponding number of parameters characterizing the sound in the window in a way consistent with the way the processing was done for the multiple training time intervals. In step 317, the processed data output by the filters are input to the trained neural network 136 . . . . Thus, in step 317, a processor configured as a neural network receives operational data that indicates a time series having a duration of at least a first duration for signals from a vibration detector collected during operation of an instance of a type of medicament or test device. As a result, a classification of the sound is output by the neural network 136.

The processor so configured generates automatically, on the neural network, classification data that classifies the operational data as a first MDDSO or not by inputting processed data, generated in steps 313 and 315 based on the operational data, into an input layer of the neural network in step 317. That is, the operational data and the training data time series are each divided into one or more time intervals in steps 313 and 303, respectively. A value for a certain parameter characterizing the sound in each time interval is determined in steps 315 and 305, respectively; and, used as an input value for each node of an input layer of the neural network in steps 317 and 307, respectively. For example, in some embodiments during step 315 or 305 the certain parameter characterizing the sound in each time interval is a power spectrum value for a particular frequency interval or a plurality of power spectrum values for a corresponding plurality of frequency intervals. In some embodiments during step 315 or 305, the certain parameter characterizing the sound in each time interval is a value for a particular cepstral coefficient interval or a plurality of values for a corresponding plurality of cepstral coefficient intervals.

In some embodiments, steps 305 and 315 use floating point arithmetic operations using any known operations. In some embodiments, steps 305 and 315 use integer or fixed point processing using any known operations. In some embodiments, steps 305 and 315 use integer operations with variable conversions from floating point values to integer values based on size of values, as explained in more detail below with reference to fixed point feature extraction. This is an advantage for smaller processors that are economically integrated into delivery or training devices for preprocessing the data.

In step 319, a signal is sent by the module 134 (or 164) to an output device, such as display 138 or speaker 845, or a remote server 160. The signal indicates the sound class. Thus, in step 319, the processor sends the classification data as a signal to an output device. In some embodiments, the output device further determines whether the MDD has been operated correctly or not, e.g., to deliver the proper dose or not, based on the sound class, and so indicates to the operator 190 or some other agent, e.g., a person evaluating operator 190. In some embodiments, the output device makes this determination of proper or improper use of the MDD, based on a series of multiple sound classes received over multiple operational time series. For example, the current MDDSO is classified as a second click indicating release of a hypodermic needle plunger that follows by several first durations a first click indicating activation of the hypodermic needle plunger recorded earlier. If the time between such clicks is too short to deliver the correct dose, then the output device determines that the MDD was used improperly, and the patient has not received enough of the medicament. This improper use is indicated by a message presented on a visual display or alarm or spoken message presented through a speaker (dependent on class or on temporal sequence of classes).

In step 321, it is determined whether there is another operational time series to collect. If so, control passes back to step 311 and following steps to collect and process the next operational time series. Otherwise the method ends. For example, after start of the collection of operational time series, no MDDSO has been yet detected or identified, control would pass back to step 311. Alternatively, after a first MDDSO is collected, but before an expected second MDDSO or third MDDSO is detected, control passes back to step 311. In contrast, after a determination is made, in step 319, that a proper or improper use of the MDD has been assessed, the process may end.

3. EXAMPLE EMBODIMENT

Figure 4A:
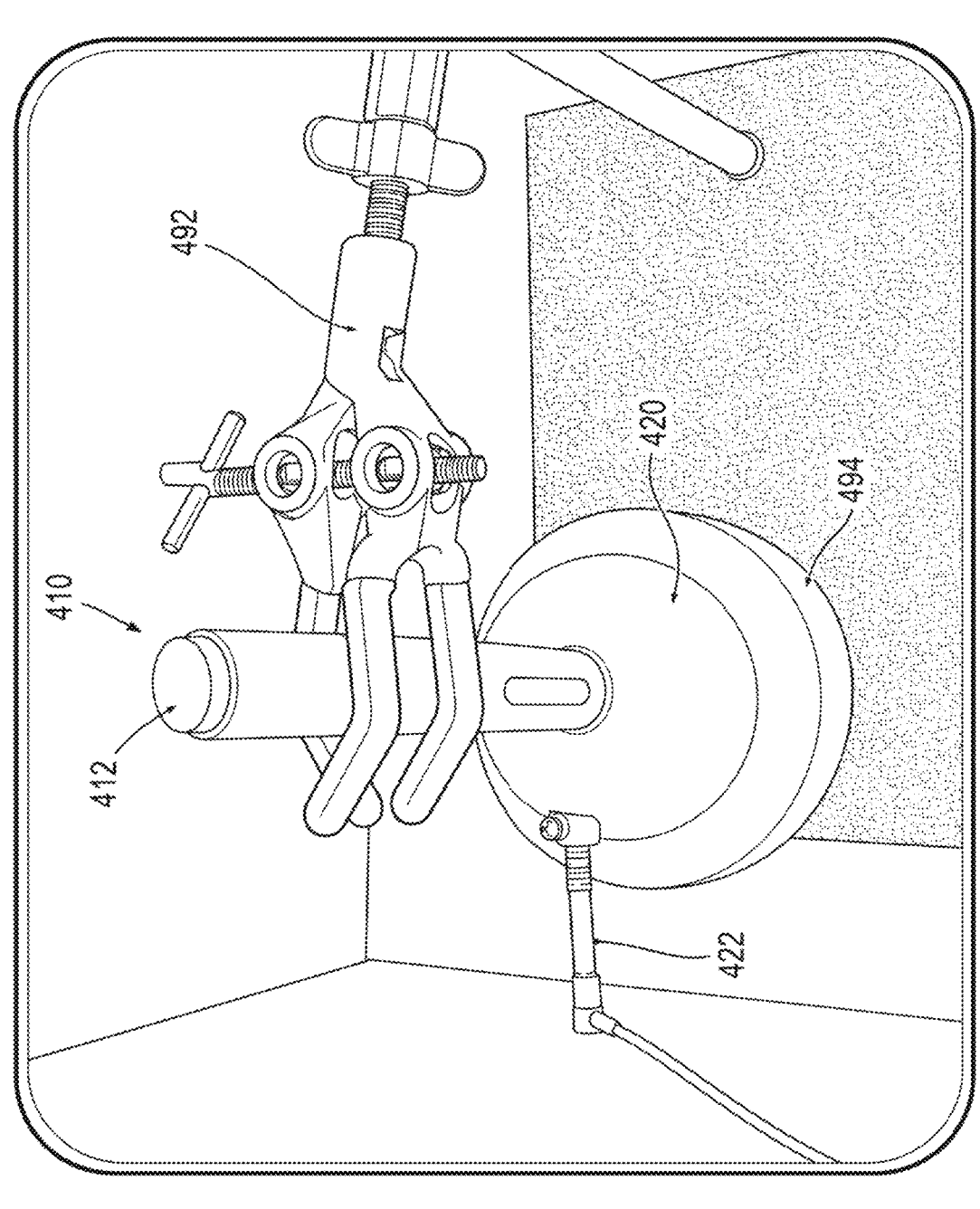
FIG. 4A is an annotated photograph that illustrates an example injection delivery device and trainer on which an example embodiment is utilized.

This section describes an experimental embodiment to be integrated into a MDD trainer 120 and developed to detect correct performance based on clicks emitted by an injection delivery device. FIG. 4A is an annotated photograph that illustrates an example injection delivery device 410 and trainer 420 for which an example embodiment is developed and utilized. The trainer 420 has an opening on the bottom through which a needle of the injection delivery device 410 can pass. The trainer housing was 3D printed using Rigur™ RG450 to allow for placement of pre-amp microphone 422 connected by wire to a software recording system (not shown). Below the trainer 420 is a material 494 (Ecoflex 00-30 silicone) that simulates the tissue density, resistance pressure and/or elasticity of skin. The injection delivery device 410 includes an operational component consisting of a button 412. The experimental setup was positioned inside an echo-free chamber. Clamp 492 holds the injection delivery device 410 in place inside trainer 420 and serves to remove operator angle of attack variability for a feasibility experiment. In other embodiments, a human operator holds the injector deliver device 410 to allow for variations in the training samples to provide more realistic recordings.

Acoustic data for training was collected in step 301 using microphone 422. Each injector training cycle acoustic recording includes a full training cycle with loading, activation (first click), release (second click), and removal from trainer, lasts about 5 seconds, and is recorded in mono (single channel) mode. In addition, each non-training cycle recording of random events (e.g., tapping on the device, moving the needle shield), called "unknown" events, lasts about 1 second, and is recorded in mono mode. A training set was generated based on 600 such full training cycle recordings; and, 400 recordings of unknown events as follows. Each training cycle recording was broken up to separate time series of first clicks, second clicks, and unknown, all of at least a first duration of 160 ms. All recording were truncated to acoustic time series with a first duration of 160 ms and resamples as needed to 16,000 samples per second (a temporal resolution of 0.0625 ms). Some of the waveforms were then modified to ensure the robustness of the trained model by varying starting time of the click or mixing in background noise from the Speech Commands Data Set, available under the Creative Commons BY 4.0 license.

Figure 4B:
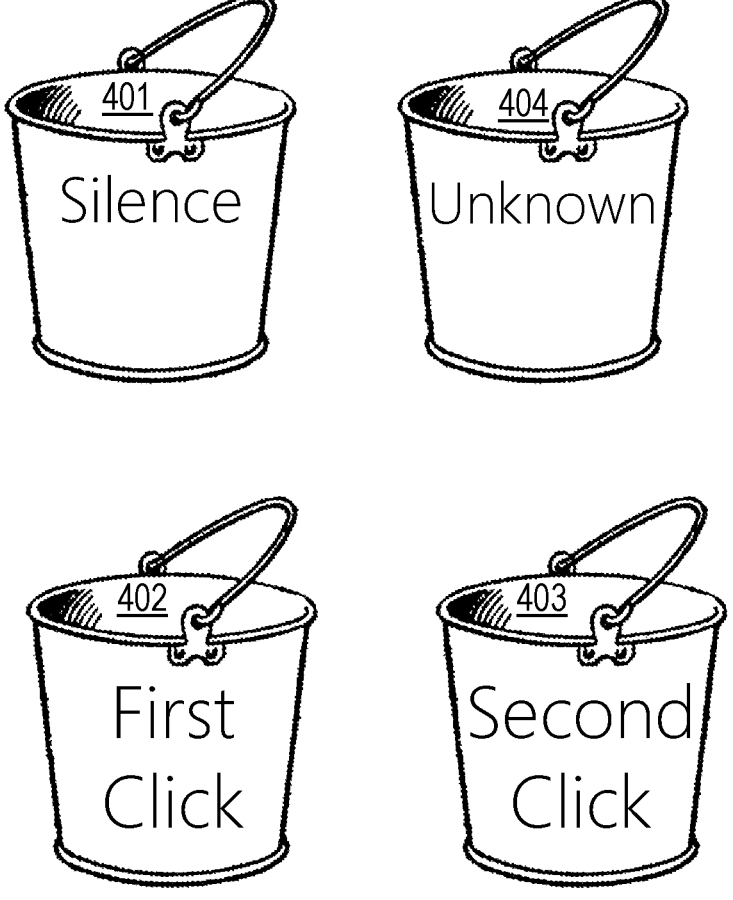
FIG. 4B is a block diagram that illustrates example MDDSO classifications, according to an embodiment.

FIG. 4B is a block diagram that illustrates example MDDSO classifications, according to an embodiment. Each time series of duration 160 ms was classified as one of four classes, silence 401, first click 402, second click 403, and unknown 404.

In step 303, called framing herein, each time series of duration 160 ms was then divided into 7 overlapping time window intervals of 40 ms with a stride of 20 ms (half the window time interval). FIG. 4C is an annotated plot that illustrates example acoustic data 442 and example first duration 441 and window time interval 443 and stride 445, according to various embodiments.

For a real-time embodiment, the classification routine is implemented using a ping-pong or circular buffer. The buffer is filled with the data from N×window shift duration. This is then passed to the classifier while the second buffer is filled. The delay between every occurrence and recognition is largely driven by the selection of N. Longer recording periods allow more time for processing but result in an increase in lag. In an example embodiments, N is advantageously selected within a range between 2 and 5. With a 20 ms shift, this is a lag of 20-100 ms.

Frequencies in a signal change over time; but, can be assumed stationary over very short time-frames. By doing Fourier transforms over these short window intervals, one can obtain a good approximation of the frequency contours of the signal. In some embodiments, the frequency spectrum of each frame (window interval) is then calculated using a Fourier transform that divides a signal into its frequency components. A Mel-filter is applied to mimic the human ear perception of sound because it is more discriminating of lower frequency sounds; and triangular filters were applied to sort the data into 40 frequency bins. Thus, in one embodiment of step 305, each interval is processed into Fourier amplitude, mel-filtered, and interpolated based on a triangular filter to obtain values for frequency bands spanning the frequency range from 0 Hz to 4 kHz. In various embodiments, the plurality of frequency intervals comprises a number of frequency intervals in a range from about 2 to about 40 frequency intervals. When the MDDSO is a click, the plurality of frequency intervals span a frequency range from about 0 Hertz to about 4 kilohertz. FIG. 4D is a block diagram that illustrates example frequency band processed data for input to a neural network, according to an embodiment. In this illustrated embodiment, there are 24 frequency bands in 7 different time intervals 451, 452, 453, 454, 455, 456, 457 producing a signature (also called a fingerprint, herein) made up of 168 cells. The darker shading in a band/interval cell indicates a smaller amplitude and lighter shading indicates a larger amplitude.

It was discovered that the previous results were highly correlated for this set of MDDSO, e.g., adjacent cells had similar values, which can present issues for machine learning algorithms, as such AI techniques are pattern seeking. To de-correlate the data, another transform is applied which yields a compressed representation of the data with emphasis on the peak frequencies. This is accomplished with a discrete cosine transform. The resulting compressed data is represented well by 12 mel-frequency cepstral coefficients (MFCC). Thus, in another embodiment of step 305, each window time interval is processed into MFCC coefficients. In various embodiments, the plurality of cepstral coefficient intervals comprises a number of cepstral coefficient intervals in a range from about 2 to about 40 cepstral coefficient intervals. When the MDDSO is a click, the plurality of cepstral coefficient intervals span a cepstral coefficient range from about 0 to about 12. FIG. 4E is a block diagram that illustrates example cepstral coefficient interval processed data for input to a neural network, according to another embodiment. There are 12 coefficients in 7 different time intervals 461, 462, 463, 464, 465, 466, 467 producing a signature (also called a fingerprint, herein) made up of 84 cells. The darker shading in a coefficient/interval cell indicates a smaller value for the coefficient and lighter shading indicates a larger value.

In step 307 a neural network 136 with 84 input nodes (84 cells of MFCC coefficient values) and 4 output nodes (silence, first click, second click, unknown) is trained with the processed data of MFCC coefficients and the known sound classes. While four classes (4 output nodes) were used during a feasibility experiment, it is anticipated that in other embodiments, depending on the implementation, it will suffice if the neural network only distinguishes between click sounds (1st or 2nd) and non-click sound (silence or unknown). In one example embodiment, the neural network includes 3 hidden layers with full connections only to the input layer and the output layer. Both CNN and DS-CNN hidden layers were used in various embodiments. Other example embodiments of neural network architecture are also trained and tested, as described in more detail below.

One fingerprint is generated for each of the 160 ms recordings of known training cycle first clicks, second clicks, intervening silence, and unknown sounds. 80%, over 1000, such fingerprints and associated classes form the training data 150. 10% are used to validate the network to ensure it is not overfit to the training data. This essentially evaluates accuracy during training. The final 10% are used for final testing to evaluate accuracy during operations.

Supervised learning was used to train this neural network. All of the fingerprints comprising the training set were labeled with the correct classes. During training, the model is corrected when it makes wrong predictions. During training, the weights and activations of the neural network are optimized. The platform TensorFlow was used to implement and train the neural network models and is available as an open source library for machine learning created by the Google Brain team.

Table 1 shows the effects on size and performance of several pre-certified neural network modules as a feasibility test before designing a particular neural network These pre-certified modules limit the processor options to ARM Cortex M0, M3, M4 or M4F with small flash memory to store the network in a range from 80 to 200 kilobytes (kB, 1 kB=$10^3$ bytes, 1 byte=8 bits). Performance of these various pre-certified modules is measured by accuracy in the validation set (10% of data available). The last three memory requirements were predicted based on the size of extant binary code.

TABLE 1

| Training neural network sizes. | | |
| --- | --- | --- |
| Neural Network architecture | Memory required for weights and activations | Accuracy in validation set performance |
| DNN, 3 fully connected | 91 kB | 90.9% |
| Single fully connected | 2.5 kB | 90.2% |
| CNN, 3 pooled | 182 kB | 91.2% |
| CNN, low latency | 171.3 kB | 93.8% |
| DS-CNN | 117.4 kB | 88.2% |

Table 1 shows that a variety of architectures can be successfully trained, even those very limited in size. This is promising for implementing the training on an embedded platform.

Table 2 shows that trained models can successfully distinguish the first and second click classes, and ignore noise from the needle shield (housing 420), when provided audio samples pre-recorded under similar conditions to the training set. For each actual class, the results are listed from most probable to least probable. For each result the confidence is given prior and posterior to iterating on the fitting process. These are the results from the classifier when run on just two clips of each type. This was used mainly to demonstrate the functionality, and how the softmax results are relayed. The confidence is the softmax output of the top three results for each of the two sounds.

TABLE 2

| Classification on experimental "operational" data set. | | | |
| --- | --- | --- | --- |
| Actual class | NN output class | Confidence A | Confidence B |
| Needle shield | Unknown | 90.9% | 98.9% |
| | First click | 8.9% | 0.7% |
| | Second click | 0.1% | 0.3% |
| First click | First click | 98.5% | 99.6% |
| | Unknown | 1.5% | 0% |
| | Second click | 0% | 0% |

TABLE 2-continued

| Classification on experimental "operational" data set. | | | |
| --- | --- | --- | --- |
| Actual class | NN output class | Confidence A | Confidence B |
| Second click | Second click | 99.9% | 96.6% |
| | First click | 0% | 1.9% |
| | Unknown | 0% | 1.4% |

A neural network for real-time click recognition (detection and classification) for an injection delivery device trainer was demonstrated based on the above results. The neural network 136 was deployed on a STM32F746NG development board that uses an ARM Cortex M7 core that is in the same family as, but more powerful than, the M3 or M4 anticipated to use ultimately. It is a single floating-point unit, with on-board LCD screen and microphones. The M7 is more capable, but still well priced, having a development board priced around $60. The audio recording works with two ping-pong buffers.

This embodiment incorporated several refinements discovered through hyperparameter optimization. A streaming audio test was developed for speed in training various network architectures. For example, a 10-minute audio stream with 277 events can conduct training in just 25 seconds. Key parameters revealed include: the frequency range advantageously spans 5 to 7000 Hz. A finer window interval of 20 ms with a smaller stride of 10 ms provides better performance. A micro-electro-mechanical system (MEMS) microphone was located and mounted on a chip set to act as the vibration detector.

Google's TENSORFLOW™ (Alphabet Inc., Mountain View, California) was used exclusively to build and train these networks. Keras is a high-level application programming interface (API) which now runs on top of TENSORFLOW™, and was integrated into TENSORFLOW™ 2.0. In other embodiments not described herein, alternatives, like the MICROSOFT™ (Microsoft Corporation, Redmond, WA) Cognitive Toolkit, were used. When training the models in TENSORFLOW™, a cross-entropy objective function, and a stochastic gradient descent method to optimize the model, were employed. Specifically, for the results presented here, an Adam optimization was used, which is based on adaptive estimation of first-order and second-order moments. According to the paper Adam: A Method for Stochastic Optimization. Kingman et al., 2015, the method is "computationally efficient, has little memory requirement, invariant to diagonal rescaling of gradients, and is well suited for problems that are large in terms of data/parameters".

Good performance was attained. After training, the neural network was run on the training data, where good results are expected, but over-fitting could be a problem, and on validation that is not subject to overfitting because this data was not used in training the network. The results on the training data set are presented in Table 3 and Table 4. The results on the validation training set are presented in Table 5 and Table 6. In a confusion matrix, the value in each cell indicates the number of audio recording intervals (not windows). Success occurs when the predicted class matches the actual class along the diagonal for each of the four classes of the example embodiment. In an ambiguity table, the correct results, false results, sensitivity, specificity, and precision are listed for each of the four classes of the example embodiment. Sensitivity (true positive rate) is defined as the proportion of actual positives that are correctly identified. Specificity (true negative rate) is defined as the proportion of actual negatives that are correctly identified. Precision is defined as the number of true positives divided by the sum of the number of true positives plus the number of false positives.

TABLE 3

| Confusion matrix for neural network results on training data | | | | |
| --- | --- | --- | --- | --- |
| Predicted class > Actual class v | Silence | Unknown | First Click | Second Click |
| Silence | 324 | 0 | 0 | 0 |
| Unknown | 2 | 2645 | 3 | 14 |
| First click | 0 | 11 | 3318 | 6 |
| Second click | 0 | 22 | 8 | 3412 |

TABLE 4

| Ambiguity Table for neural network results on training data. | | | | | | | |
| --- | --- | --- | --- | --- | --- | --- | --- |
| | False Positive | True Positive | True Negative | False Negative | Sensitivity | Specificity | Precision |
| Silence | 2 | 324 | 9375 | 0 | 100.00% | 99.98% | 99.39% |
| Unknown | 33 | 2645 | 7054 | 19 | 99.29% | 99.53% | 98.77% |
| First click | 11 | 3318 | 6381 | 17 | 99.49% | 99.83% | 99.67% |
| Second click | 20 | 3412 | 6287 | 30 | 99.13% | 99.68% | 99.42% |
| Overall | 66 | 9699 | 29097 | 66 | 99.32% | 99.77 % | 99.32% |

TABLE 5

| Confusion matrix for neural network results on validation data | | | | |
| --- | --- | --- | --- | --- |
| Predicted class > Actual class v | Silence | Unknown | First Click | Second Click |
| Silence | 45 | 0 | 0 | 0 |
| Unknown | 0 | 462 | 0 | 7 |
| First click | 0 | 1 | 494 | 4 |
| Second click | 0 | 1 | 1 | 397 |

TABLE 6

| Ambiguity Table for neural network results on validation data. | | | | | | | |
| --- | --- | --- | --- | --- | --- | --- | --- |
| | False Positive | True Positive | True Negative | False Negative | Sensitivity | Specificity | Precision |
| Silence | 0 | 45 | 1353 | 0 | 100.00% | 100.00% | 100.00% |
| Unknown | 2 | 462 | 936 | 7 | 98.51% | 99.79% | 99.57% |
| First click | 1 | 494 | 904 | 5 | 99.00% | 99.89% | 99.80% |
| Second click | 11 | 397 | 1001 | 2 | 99.50% | 98.91% | 97.30% |
| Overall | 14 | 1398 | 4194 | 14 | 99.01% | 99.67% | 99.01% |

Figure 5A:
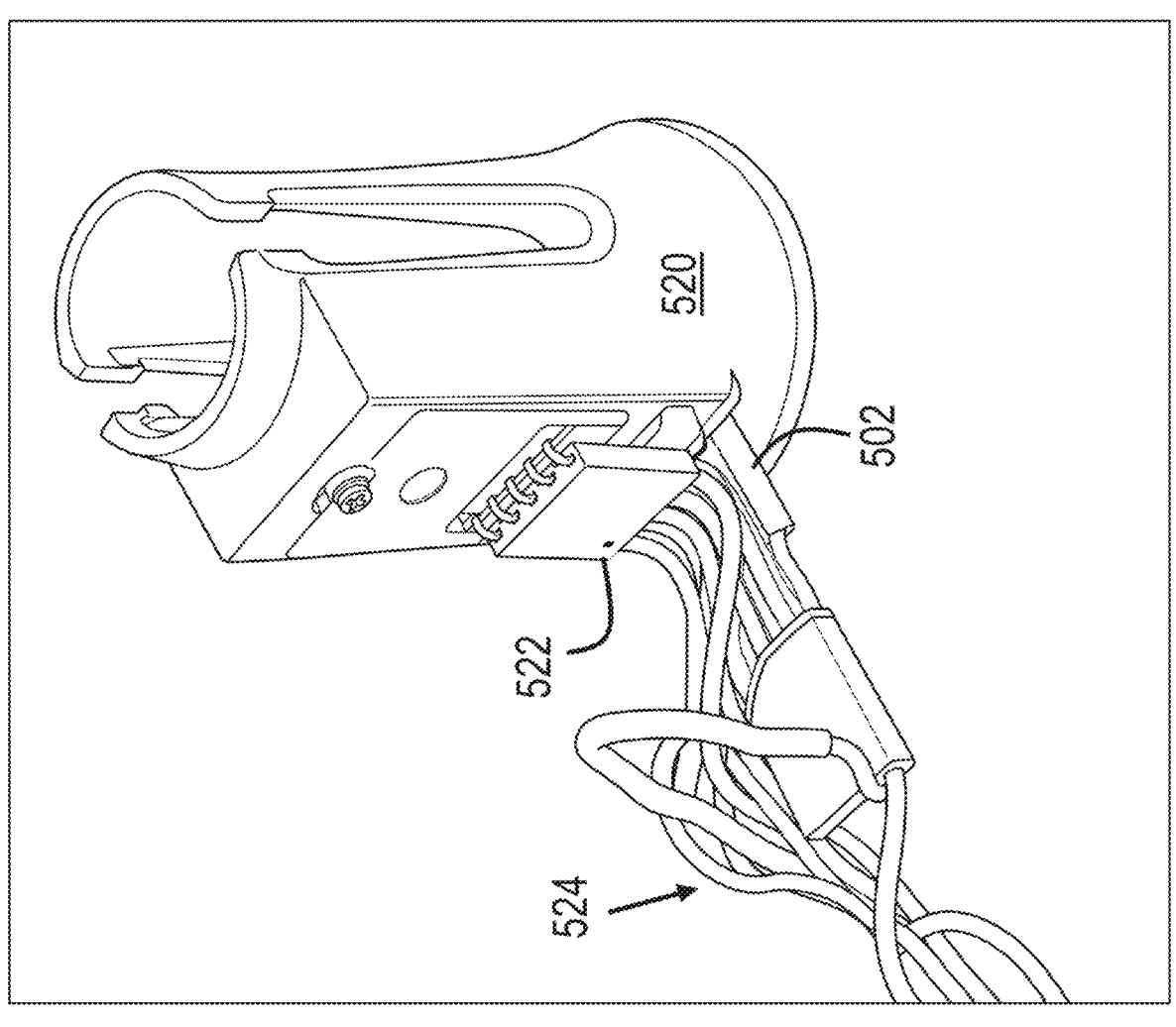
Figure 5B:
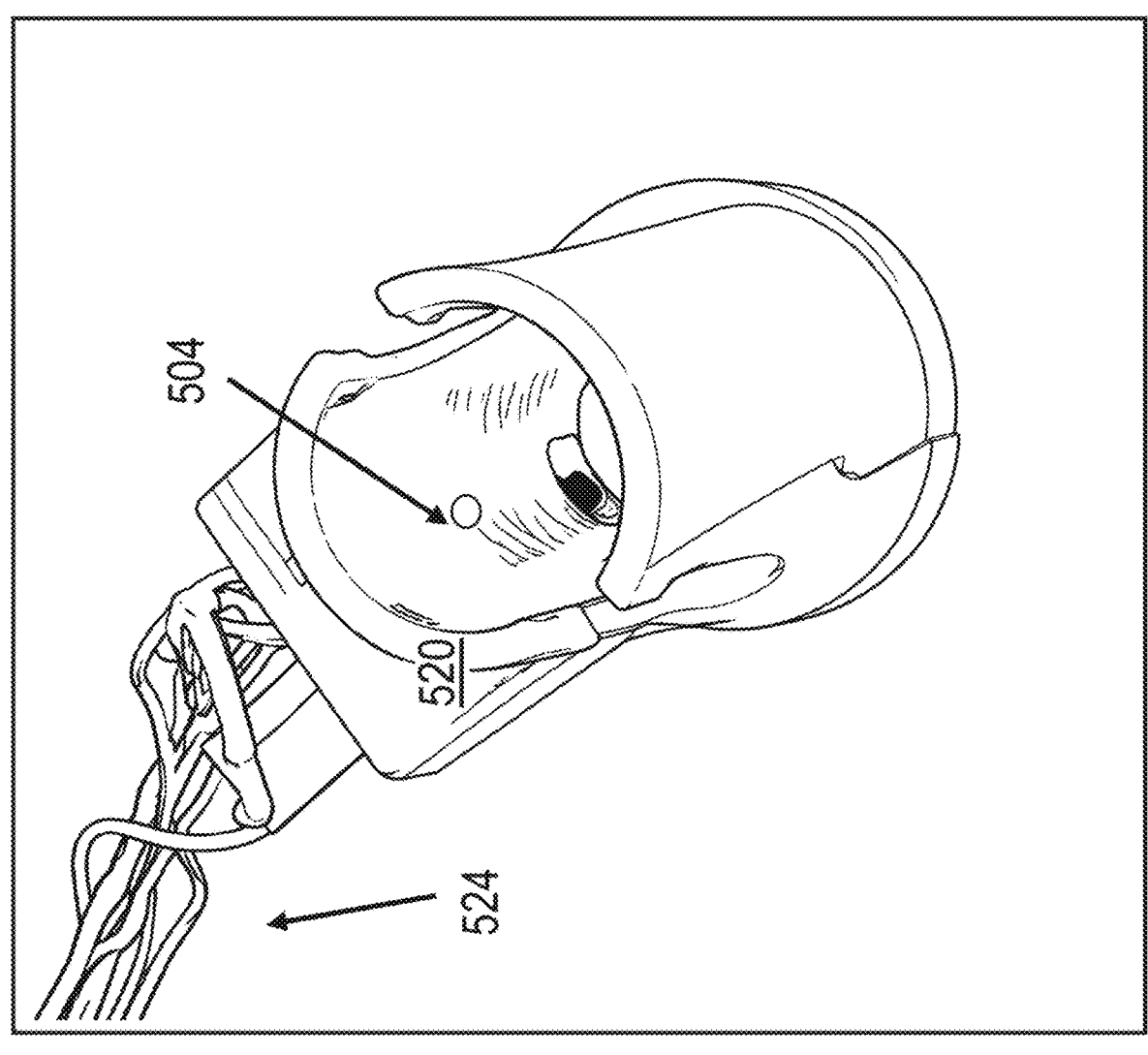

FIG. 5A through FIG. 5C are annotated photographs that illustrate example components of a medicament delivery device trainer apparatus, according to an experimental embodiment. FIG. 5A shows an injection device trainer 520 with one or more non-acoustic sensors for ADHEREIT™ (Noble, an APTAR PHARMA™ company, Orlando, Florida) to function. A microphone daughter board is disposed on the trainer 520 and connected to wiring 522. A capacitive sensor daughter board is disposed in the trainer 520 connected to wiring 502. Connectors 524 provide data communications or power or some combination with an external output device, such as a tablet or other mobile device. FIG. 5B shows an injection device trainer 520 with interior opening to expose microphone 504; and, shows connectors 524. FIG. 5C shows a layout with the modified trainer 520 and connectors 524 running to an output device 530 and power cable 561. The output device indicates the status of the trainer is one of "holding" or "read" or "injection start" (first click) or "injection complete" (second click). Also shown is a sound calibration device 590, which is not part of the system embodiment; but, was used to demonstrate the system's ability to ignore loud external noise.

In the example embodiments described above, the Fast Fourier Transform and Mel-frequency cepstral coefficients (MFCC) are calculated in floating point, taking advantage of the floating-point capabilities in the demonstration microcontrollers. More economical chipsets used in some low-cost, disposable embodiments, do not have floating point capabilities. In such embodiments, it is advantageous to have a fixed-point preprocessor, comparable in accuracy to the current floating-point version. Thus, in some embodiments, step 305 uses integer operations with variable conversions from floating point values to integer values based on size of values.

In various embodiments, this conversion can be performed at any data processing stage prior to providing as a fixed bit (e.g., 8 bit) value to each input node of the neural network for training, and in a similar way during operation after such training. The neural network output classification is naturally one or more nodes of few bits, representing a small finite number of classifications.

With fixed-point notation that uses integers, the gaps between adjacent numbers always equal a value of one. This can cause significant issues in data analysis if assumptions about the anticipated data are incorrect. Conversely, in floating-point notation, gaps between adjacent numbers are not uniformly spaced. The gap between any two numbers is many orders of magnitude smaller than the value of the numbers (approximately ten million times smaller for ANSI/IEEE Std. 754 standard format, with large gaps between large numbers and small gaps between small numbers The exponentiation inherent in floating-point computation assures a much larger dynamic range (i.e., the difference between largest and smallest numbers that can be represented), which is especially important when processing extremely variable data sets where the range may be unpredictable (like live audio). As such, floating-point processors are ideally suited for computationally intensive applications.

It is also important to consider fixed and floating-point formats in the context of precision, the size of the gaps between numbers. Every time a digital signal processor (DSP) generates a new number via a mathematical calculation, that number must be rounded to the nearest value that can be stored via the format in use. Rounding and/or truncating numbers during signal processing produces a deviation between actual analog values and digital values, yielding noise or error in the result. Since the gaps between adjacent numbers can be much larger with fixed-point processing when compared to floating-point processing, round-off error can be much more pronounced. As such, floating-point processing yields much greater precision than fixed-point processing, distinguishing floating-point processors as ideal for dynamic signal processing, where computational accuracy is a critical requirement.

Dynamic range and precision considerations are why the current AdhereIT preprocessor uses floating-point calculations. The data coming from the microphone has a large dynamic range of ≈95 dB. For fixed-point calculations, increasing the range has a negative impact on the precision.

To balance the precision of floating point with the efficiency of fixed point, some embodiments use fractional fixed-point format, also known as Q-format. Q-format is a binary fixed point number format where the number of fractional bits is specified. For example, a 16-bit integer can be represented as Q0.15, a number which has 15 fractional bits, or a Q1.14 number which has 1 integer bit and 14 fractional bits. In both cases the sign occupies one of the bits. The format for these numbers is Qm.n, where the range is defined as $[-(2^{m-1}), 2^{m-1}-2^{-n}]$ and the resolution is $2^{-n}$. As the range increases, the resolution decreases.

A single range for all fixed-point calculations would lower the resolution, dramatically and negatively impacting the accuracy of the computations. As an example, the MFCC computation results in a range of numbers from 80 to 6.5E-06. To accommodate this range with a single format, one would need to choose Q7.8, thus providing a resolution of 0.0039 or 600× the smallest value in the range. Thus, several small values would fall to zero.

To account for the varying range of our data, a low cost embedded system embodiment is designed to track the Q format of each member of the dataset through the series of fixed-point calculations required to complete pre-processing. This tracking information is used to adjust how each calculation is performed, how each intermediate result is formatted, and how the final pre-processor MFCC is scaled for input into the neural network. For example, different rules need to be applied if two numbers are of different format, or if the result requires a format change. This system for tracking a data set of Q-format numbers as they are processed was developed to enable low-cost applications.

Consider for example a dataset with large dynamic range having the floating-point values listed in Table 7.

TABLE 7

| Sample dataset with large dynamic range. Floating Point | |
| --- | --- |
| 3526.92 | 130.429 |
| 1.15689 | 6.49069E−05 |

If the Q format is not varied for each value, the need to accommodate the largest value, 3526.92, involves a format of Q12.3. Converting each number to an integer (quantized number) by multiplying by a power of two to eliminate any fraction and yield the same relative size based on this format, one gets the quantized number shown in table 8A. Each number has the same format as indicated in Table 8B. But when converted back from the integer to the floating point using the associated Q format, precision is lost, as shown in Table 8C.

TABLE 8

| Single Q format loses precision | | | | | |
| --- | --- | --- | --- | --- | --- |
| 8A. Quantized Number | | 8B. Qm.n tracking | | 8C. Conversion to Float | |
| 28215 | 1043 | Q12.3 | Q12.3 | 3526.88 | 130.375 |
| 9 | 0 | Q12.3 | Q12.3 | 1.125 | 0 |

In the Q format tracking method used in some embodiments, each value is scaled independently and its associated Q format is tracked, preserving the information in the smaller numbers, as shown in Table 9, which was lost in Table 8.

TABLE 9

| Tracking Q format preserves precision | | | | | |
| --- | --- | --- | --- | --- | --- |
| 9A. Quantized Number | | 9B. Qm.n tracking | | 9C. Conversion to Float | |
| 28215 | 16695 | Q12.3 | Q8.7 | 3526.88 | 130.430 |
| 18954 | 2 | Q1.14 | Q0.15 | 1.15686 | 6.10351E−05 |

When all operands in a particular operation have the same Q format, no conversion is done. However, when different operands have different Q formats, the difference in Q-formats is used to interpret the result. Using this tracking method to convert the data before each operation performed in the preprocessor to use only fixed-point calculations, such embodiments were able to maintain 99.9992% alignment in calculations between fixed- and floating-point results, while using much less powerful processors. In an example embodiment, the change to Q-format and fixed point processing allowed for the following reductions: a reduction of 2.667 in Flash memory size; a reduction of 2.667 in RAM size; a reduction of 3.4 times in cost; and, a reductions of 2% in DMIPS/MHz processor speed.

4. COMPUTATIONAL HARDWARE OVERVIEW

FIG. 6 is a block diagram that illustrates a computer system 600 upon which an embodiment of the invention may be implemented. Computer system 600 includes a communication mechanism such as a bus 610 for passing information between other internal and external components of the computer system 600. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 600, or a portion thereof, constitutes a means for performing one or more steps of one or more methods described herein.

A sequence of binary digits constitutes digital data that is used to represent a number or code for a character. A bus 610 includes many parallel conductors of information so that information is transferred quickly among devices coupled to the bus 610. One or more processors 602 for processing information are coupled with the bus 610. A processor 602 performs a set of operations on information. The set of operations include bringing information in from the bus 610 and placing information on the bus 610. The set of operations also typically include comparing two or more units of information, shifting positions of units of information, and combining two or more units of information, such as by addition or multiplication. A sequence of operations to be executed by the processor 602 constitutes computer instructions.

Computer system 600 also includes a memory 604 coupled to bus 610. The memory 604, such as a random access memory (RAM) or other dynamic storage device, stores information including computer instructions. Dynamic memory allows information stored therein to be changed by the computer system 600. RAM allows a unit of information stored at a location called a memory address to be stored and retrieved independently of information at neighboring addresses. The memory 604 is also used by the processor 602 to store temporary values during execution of computer instructions. The computer system 600 also includes a read only memory (ROM) 606 or other static storage device coupled to the bus 610 for storing static information, including instructions, that is not changed by the computer system 600. Also coupled to bus 610 is a non-volatile (persistent) storage device 608, such as a magnetic disk or optical disk, for storing information, including instructions, that persists even when the computer system 600 is turned off or otherwise loses power.

Information, including instructions, is provided to the bus 610 for use by the processor from an external input device 612, such as a keyboard containing alphanumeric keys operated by a human user, or a sensor. A sensor detects conditions in its vicinity and transforms those detections into signals compatible with the signals used to represent information in computer system 600. Other external devices coupled to bus 610, used primarily for interacting with humans, include a display device 614, such as a cathode ray tube (CRT) or a liquid crystal display (LCD), for presenting images, and a pointing device 616, such as a mouse or a trackball or cursor direction keys, for controlling a position of a small cursor image presented on the display 614 and issuing commands associated with graphical elements presented on the display 614.

In the illustrated embodiment, special purpose hardware, such as an application specific integrated circuit (IC) 620, is coupled to bus 610. The special purpose hardware is configured to perform operations not performed by processor 602 quickly enough for special purposes. Examples of application specific ICs include graphics accelerator cards for generating images for display 614, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 600 also includes one or more instances of a communications interface 670 coupled to bus 610. Communication interface 670 provides a two-way communication coupling to a variety of external devices that operate with their own processors, such as printers, scanners and external disks. In general the coupling is with a network link 678 that is connected to a local network 680 to which a variety of external devices with their own processors are connected. For example, communication interface 670 may be a parallel port or a serial port or a universal serial bus (USB) port on a personal computer. In some embodiments, communications interface 670 is an integrated services digital network (ISDN) card or a digital subscriber line (DSL) card or a telephone modem that provides an information communication connection to a corresponding type of telephone line. In some embodiments, a communication interface 670 is a cable modem that converts signals on bus 610 into signals for a communication connection over a coaxial cable or into optical signals for a communication connection over a fiber optic cable. As another example, communications interface 670 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 670 sends and receives electrical, acoustic or electromagnetic signals, including infrared and optical signals, that carry information streams, such as digital data.

The term computer-readable medium is used herein to refer to any medium that participates in providing information to processor 602, including instructions for execution. Such a medium may take many forms, including, but not limited to, non-volatile media, volatile media and transmission media. Non-volatile media include, for example, optical or magnetic disks, such as storage device 608. Volatile media include, for example, dynamic memory 604. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 602, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 602, except for carrier waves and other signals.

Logic encoded in one or more tangible media includes one or both of processor instructions on a computer-readable storage media and special purpose hardware, such as ASIC 420.

Network link 678 typically provides information communication through one or more networks to other devices that use or process the information. For example, network link 678 may provide a connection through local network 680 to a host computer 682 or to equipment 684 operated by an Internet Service Provider (ISP). ISP equipment 684 in turn provides data communication services through the public, world-wide packet-switching communication network of networks now commonly referred to as the Internet 690. A computer called a server 692 connected to the Internet provides a service in response to information received over the Internet. For example, server 692 provides information representing video data for presentation at display 614.

The invention is related to the use of computer system 600 for implementing the techniques described herein. According to one embodiment of the invention, those techniques are performed by computer system 600 in response to processor 602 executing one or more sequences of one or more instructions contained in memory 604. Such instructions, also called software and program code, may be read into memory 604 from another computer-readable medium such as storage device 608. Execution of the sequences of instructions contained in memory 604 causes processor 602 to perform the method steps described herein. In alternative embodiments, hardware, such as application specific integrated circuit 620, may be used in place of or in combination with software to implement the invention. Thus, embodiments of the invention are not limited to any specific combination of hardware and software.

The signals transmitted over network link 678 and other networks through communications interface 670, carry information to and from computer system 600. Computer system 600 can send and receive information, including program code, through the networks 680, 690 among others, through network link 678 and communications interface 670. In an example using the Internet 690, a server 692 transmits program code for a particular application, requested by a message sent from computer 600, through Internet 690, ISP equipment 684, local network 680 and communications interface 670. The received code may be executed by processor 602 as it is received, or may be stored in storage device 608 or other non-volatile storage for later execution, or both. In this manner, computer system 600 may obtain application program code in the form of a signal on a carrier wave.

Various forms of computer readable media may be involved in carrying one or more sequence of instructions or data or both to processor 602 for execution. For example, instructions and data may initially be carried on a magnetic disk of a remote computer such as host 682. The remote computer loads the instructions and data into its dynamic memory and sends the instructions and data over a telephone line using a modem. A modem local to the computer system 600 receives the instructions and data on a telephone line and uses an infra-red transmitter to convert the instructions and data to a signal on an infra-red a carrier wave serving as the network link 678. An infrared detector serving as communications interface 670 receives the instructions and data carried in the infrared signal and places information representing the instructions and data onto bus 610. Bus 610 carries the information to memory 604 from which processor 602 retrieves and executes the instructions using some of the data sent with the instructions. The instructions and data received in memory 604 may optionally be stored on storage device 608, either before or after execution by the processor 602.

FIG. 7 illustrates a chip set 700 upon which an embodiment of the invention may be implemented. Chip set 700 is programmed to perform one or more steps of a method described herein and includes, for instance, the processor and memory components described with respect to FIG. 6 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 700, or a portion thereof, constitutes a means for performing one or more steps of a method described herein.

In one embodiment, the chip set 700 includes a communication mechanism such as a bus 701 for passing information among the components of the chip set 700. A processor 703 has connectivity to the bus 701 to execute instructions and process information stored in, for example, a memory 705. The processor 703 may include one or more processing cores with each core configured to perform independently. A multi-core processor enables multiprocessing within a single physical package. Examples of a multi-core processor include two, four, eight, or greater numbers of processing cores. Alternatively or in addition, the processor 703 may include one or more microprocessors configured in tandem via the bus 701 to enable independent execution of instructions, pipelining, and multithreading. The processor 703 may also be accompanied with one or more specialized components to perform certain processing functions and tasks such as one or more digital signal processors (DSP) 707, or one or more application-specific integrated circuits (ASIC) 709. A DSP 707 typically is configured to process real-world signals (e.g., sound) in real time independently of the processor 703. Similarly, an ASIC 709 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 703 and accompanying components have connectivity to the memory 705 via the bus 701. The memory 705 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 705 also stores the data associated with or generated by the execution of one or more steps of the methods described herein.

FIG. 8 is a diagram of example components of a mobile terminal 800 (e.g., cell phone handset) for communications, which is capable of operating in the system of FIG. 2B, according to one embodiment. In some embodiments, mobile terminal 801, or a portion thereof, constitutes a means for performing one or more steps described herein. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 803, a Digital Signal Processor (DSP) 805, and a receiver/transmitter unit including a microphone gain control unit and a speaker gain control unit. A main display unit 807 provides a display to the user in support of various applications and mobile terminal functions that perform or support the steps as described herein. The display 807 includes display circuitry configured to display at least a portion of a user interface of the mobile terminal (e.g., mobile telephone). Additionally, the display 807 and display circuitry are configured to facilitate user control of at least some functions of the mobile terminal. An audio function circuitry 809 includes a microphone 811 and microphone amplifier that amplifies the speech signal output from the microphone 811. The amplified speech signal output from the microphone 811 is fed to a coder/decoder (CODEC) 813.

A radio section 815 amplifies power and converts frequency in order to communicate with a base station, which is included in a mobile communication system, via antenna 817. The power amplifier (PA) 819 and the transmitter/modulation circuitry are operationally responsive to the MCU 803, with an output from the PA 819 coupled to the duplexer 821 or circulator or antenna switch, as known in the art. The PA 819 also couples to a battery interface and power control unit 820.

In use, a user of mobile terminal 801 speaks into the microphone 811 and his or her voice along with any detected background noise is converted into an analog voltage. The analog voltage is then converted into a digital signal through the Analog to Digital Converter (ADC) 823. The control unit 803 routes the digital signal into the DSP 805 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 825 for compensation of any frequency-dependent impairments that occur during transmission though the air such as phase and amplitude distortion. After equalizing the bit stream, the modulator 827 combines the signal with a RF signal generated in the RF interface 829. The modulator 827 generates a sine wave by way of frequency or phase modulation. In order to prepare the signal for transmission, an up-converter 831 combines the sine wave output from the modulator 827 with another sine wave generated by a synthesizer 833 to achieve the desired frequency of transmission. The signal is then sent through a PA 819 to increase the signal to an appropriate power level. In practical systems, the PA 819 acts as a variable gain amplifier whose gain is controlled by the DSP 805 from information received from a network base station. The signal is then filtered within the duplexer 821 and optionally sent to an antenna coupler 835 to match impedances to provide maximum power transfer. Finally, the signal is transmitted via antenna 817 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 801 are received via antenna 817 and immediately amplified by a low noise amplifier (LNA) 837. A down-converter 839 lowers the carrier frequency while the demodulator 841 strips away the RF leaving only a digital bit stream. The signal then goes through the equalizer 825 and is processed by the DSP 805. A Digital to Analog Converter (DAC) 843 converts the signal and the resulting output is transmitted to the user through the speaker 845, all under control of a Main Control Unit (MCU) 803 which can be implemented as a Central Processing Unit (CPU) (not shown).

The MCU 803 receives various signals including input signals from the keyboard 847. The keyboard 847 and/or the MCU 803 in combination with other user input components (e.g., the microphone 811) comprise a user interface circuitry for managing user input. The MCU 803 runs a user interface software to facilitate user control of at least some functions of the mobile terminal 801 as described herein. The MCU 803 also delivers a display command and a switch command to the display 807 and to the speech output switching controller, respectively. Further, the MCU 803 exchanges information with the DSP 805 and can access an optionally incorporated SIM card 849 and a memory 851. In addition, the MCU 803 executes various control functions required of the terminal. The DSP 805 may, depending upon the implementation, perform any of a variety of conventional digital processing functions on the voice signals. Additionally, DSP 805 determines the background noise level of the local environment from the signals detected by microphone 811 and sets the gain of microphone 811 to a level selected to compensate for the natural tendency of the user of the mobile terminal 801.

The CODEC 813 includes the ADC 823 and DAC 843. The memory 851 stores various data including call incoming tone data and is capable of storing other data including music data received via, e.g., the global Internet. The software module could reside in RAM memory, flash memory, registers, or any other form of writable storage medium known in the art. The memory device 851 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 849 carries, for instance, important information, such as the cellular phone number, the carrier supplying service, subscription details, and security information. The SIM card 849 serves primarily to identify the mobile terminal 801 on a radio network. The card 849 also contains a memory for storing a personal telephone number registry, text messages, and user specific mobile terminal settings.

In some embodiments, the mobile terminal 801 includes a digital camera comprising an array of optical detectors, such as charge coupled device (CCD) array 865. The output of the array is image data that is transferred to the MCU for further processing or storage in the memory 851 or both. In the illustrated embodiment, the light impinges on the optical array through a lens 863, such as a pin-hole lens or a material lens made of an optical grade glass or plastic material. In the illustrated embodiment, the mobile terminal 801 includes a light source 861, such as a LED to illuminate a subject for capture by the optical array, e.g., CCD 865. The light source is powered by the battery interface and power control module 820 and controlled by the MCU 803 based on instructions stored or loaded into the MCU 803.

4. ALTERNATIVES, DEVIATIONS AND MODIFICATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

5. REFERENCES

All the references listed here are hereby incorporated by reference as if fully set forth herein except for terminology inconsistent with that used herein.

Abadi, M. et al "Large scale Machine Learning on Heterogeneous Distributed Systems," Google Research whitepaper, Alphabet, Mountain View, CA, USA, 2015;

Jagtap, R. "Adding Intelligent Vision to Your Next Embedded Product," ARM whitepaper. ARM Ltd, Cambridge, UK, 2019;

Kingman, D. P., and J. Leik Ba, "ADAM: A Method for Stochastic Optimization," published as conference paper at International Conference on Learning Representations (ICLR) 2015;

Lai, L., N. Suda, V. Chandra, "CMSIS-NN: Efficient Neural Network Kernals for ARM Cortex-M CPUs," ARM whitepaper. ARM Ltd, Cambridge, UK, 2018;

Lai, L., N. Suda, V. Chandra, "Deep Convolutional Neural Network Inference with Floating-point Weights and Fixed-point Activations," ARM whitepaper. ARM Ltd, Cambridge, UK, 2017;

Shore, C. "Think Local: How to Migrate Intelligences from the Cloud to Embedded Devices at the Edge," ARM whitepaper. ARM Ltd, Cambridge, UK, 2019;

Suda, N. "Machine Learning on ARM Cortex-M Microcontrollers," ARM whitepaper. ARM Ltd, Cambridge, UK, 2019;

Zhang, Y., N. Suda, L. lai, V. Chandra, "Hello Edge: keyword Spotting on Microcontrollers," ARM whitepaper. ARM Ltd, Cambridge, UK, 2018;

Zhang, Y., N. Suda, L. Lai, V. Chandra, "The Powers of Speech: Supporting Voice-Driven Commands in Small, Low-Power Microcontrollers," ARM whitepaper. ARM Ltd, Cambridge, UK, 2018.

What is claimed is:

1. A method for artificial intelligence medicament or test delivery device sound output (MDDSO) detection, comprising:

providing a medicament or test delivery device (MDD) comprising an operational component to be manually operated by an operator undergoing training for administering a medicament, with one or more distinct sounds being emitted in response to the operator operating the operational component, and with the medicament or test delivery device corresponding to a first type;

generating by a vibration detector a time series of acoustic data in response to receiving the one or more emitted distinct sounds;

receiving, at a processor configured as a neural network, operational data that includes the time series of acoustic data as having a duration of at least a first duration;

generating automatically on the neural network classification data that classifies the operational data as a first MDDSO or not by inputting processed data based on the operational data into an input layer of the neural network; and sending the classification data to an output device, with the classification data providing feedback to the operator to indicate whether the first type of medicament or test delivery device was correctly operated when the operational data is classified as the first MDDSO, with the feedback being in terms of at least one of resistance pressure, measure of an amount of medicament delivered, and detect proper forces and sequence on operation of the operational component, and to display a pass or fail result;

wherein prior to receiving the operational data, the neural network has been trained based on the following:

collecting a first training time series corresponding to first training data that indicates a plurality of time series of ambient sounds, each first training time series having the first duration, collecting a second training time series corresponding to second training data that indicates a plurality of time series of sound having the first duration during operation of the first type of medicament or test delivery device, each second training time series of the second training data includes sound from the first MDDSO emitted from the first type of medicament or test delivery device, dividing the first duration of the first training data and the second training data into one or more window intervals, processing each window interval into one or more values for a corresponding number of parameters characterizing sound, processing acoustic time series data in each window interval to produce one or more values for a corresponding number of parameters characterizing sound in the window interval, and providing the processed acoustic time series data in each window interval to an input layer of the neural network, and with an output layer of the neural network to produce correct classification data for the one or more values of the processed acoustic time series data provided to the input layer.

2. The method as recited in claim 1, wherein:

prior to receiving the operational data, the neural network has been trained further with third training data that indicates a plurality of time series of ambient sound having the first duration during operation of the first type of medicament or test delivery device, wherein each time series of the third training data includes sound from a different second MDDSO emitted from the first type of medicament or test delivery device, wherein the second MDDSO follows in time the first MDDSO during normal operation of the first type of medicament or test delivery device; and the classification data further classifies the operational data as the first MDDSO or the second MDDSO or neither.

3. The method as recited in claim 2, wherein:

prior to receiving the operational data, the neural network has been trained further with fourth training data that indicates a plurality of time series of ambient sound having the first duration during operation of the first type of medicament or test delivery device, wherein each time series of the fourth training data includes sound from a different third MDDSO emitted from the first type of medicament or test delivery device, wherein the third MDDSO follows in time the first MDDSO during normal operation of the first type of medicament or test delivery device; and the classification data further classifies the operational data as the first MDDSO or the second MDDSO or the third MDDSO or none.

4. The method as recited in claim 1, wherein the certain parameter characterizing the sound in each time interval is a power spectrum value for a particular frequency interval.

5. The method as recited in claim 4, wherein the power spectrum value for a particular frequency interval is a plurality of power spectrum values for a corresponding plurality of frequency intervals.

6. The method as recited in claim 5, wherein the plurality of frequency intervals comprises a number of frequency intervals in a range from about 2 to about 40 frequency intervals.

7. The method as recited in claim 6, wherein:

the MDDSO is a click; and the plurality of frequency intervals spans a frequency range from about 0 Hertz to about 4 kilohertz.

8. The method as recited in claim 1, wherein the certain parameter characterizing the sound in each time interval is a value for a particular cepstral coefficient interval.

9. The method as recited in claim 8, wherein the value for a particular cepstral coefficient interval is a plurality of values for a corresponding plurality of cepstral coefficient intervals.

10. The method as recited in claim 9, wherein the plurality of cepstral coefficient intervals comprises a number of cepstral coefficient intervals in a range from about 2 to about 40 cepstral coefficient intervals, wherein, optionally, the MDDSO is a click; and the plurality of cepstral coefficient intervals spans a cepstral coefficient range from about 0 to about 12.

11. The method as recited in claim 1, wherein the certain parameter characterizing the sound in each time interval is a value output by a particular filter.

12. The method as recited in claim 11, wherein the value output by the particular filter is a plurality of values output by a corresponding plurality of filters.

13. The method as recited in claim 12, wherein the plurality of filters comprises about 10 to about 60 filters.

14. The method as recited in claim 12, wherein the plurality of filters comprises about 20 to about 40 filters.

15. The method as recited in claim 1, wherein the first duration is selected in a range from 10 milliseconds to 2000 milliseconds.

16. The method as recited in claim 1, wherein the first duration is selected in a range from 10 milliseconds to 2000 milliseconds and each time interval is selected in a range from 10 milliseconds to 130 milliseconds and the time interval is less than or equal to the first duration.

17. The method as recited in claim 1, wherein:

prior to receiving the operational data, the neural network has been trained further with third training data that indicates a plurality of time series of ambient sound having the first duration during operation of a different second type of medicament or test delivery device, wherein each time series of the third training data includes sound from a different second MDDSO emitted from the second type of medicament or test delivery device; and the classification data further classifies the operational data as the first type of medicament or test delivery device or the second type of medicament or test delivery device or neither.

18. The method as recited in claim 1, further comprising, before receiving the operational data, performing the steps of:

receiving information indicating a type of medicament or test delivery device; and retrieving configuration data that indicates configuration of the neural network for the type of medicament or test delivery device; and configuring the processor based on the configuration data as the neural network for the type of medicament or test delivery device.

19. A non-transitory computer-readable medium carrying one or more sequences of instructions, wherein execution of the one or more sequences of instructions by one or more processors configured as a neural network causes the one or more processors to perform the following steps:

receiving operational data that indicates a time series having a duration of at least a first duration for a signal from a vibration detector collected during operation of an instance of a type of medicament or test delivery device, with the type of medicament or test delivery device includes an operational component being operated by an operator undergoing training for administering a medicament;

generating classification data that classifies the operational data as a first medicament or test delivery device sound output (MDDSO) or not by inputting processed data based on the operational data into an input layer of the neural network; and sending the classification data as a signal to an output device, with the classification data providing feedback to an operator of the type of medicament or test delivery device (MDD) to indicate whether the type of medicament or test delivery device was correctly operated when the operational data is classified as the first MDDSO, with the feedback being in terms of at least one of resistance pressure, measure of an amount of medicament delivered, and detect proper forces and sequence on operation of the operational component, and to display a pass or fail result;

wherein prior to receiving the operational data, the neural network has been trained based on the following:

collecting a first training time series corresponding to first training data that indicates a plurality of time series of ambient sounds, each first training time series having the first duration, collecting a second training time series corresponding to second training data that indicates a plurality of time series of sound having the first duration during operation of the first type of medicament or test delivery device, each second training time series of the second training data includes sound from the first MDDSO emitted from the first type of medicament or test delivery device, dividing the first duration of the first training data and the second training data into one or more window intervals, processing each window interval into one or more values for a corresponding number of parameters characterizing sound, processing acoustic time series data in each window interval to produce one or more values for a corresponding number of parameters characterizing sound in the window interval, and providing the processed acoustic time series data in each window interval to an input layer of the neural network, and with an output layer of the neural network to produce correct classification data for the one or more values of the processed acoustic time series data provided to the input layer.

* * * * *